US011707513B2

(12) United States Patent
Biolchi et al.

(10) Patent No.: US 11,707,513 B2
(45) Date of Patent: *Jul. 25, 2023

(54) MENINGOCOCCUS VACCINES

(71) Applicant: GLAXOSMITHKLINE BIOLOGICALS, SA, Rixensart (BE)

(72) Inventors: Alessia Biolchi, Siena (IT); Brunella Brunelli, Siena (IT); Marzia Monica Giuliani, Siena (IT); Vega Masignani, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 283 days.

This patent is subject to a terminal disclaimer.

(21) Appl. No.: 15/319,665

(22) PCT Filed: Jul. 16, 2015

(86) PCT No.: PCT/EP2015/066229

§ 371 (c)(1),
(2) Date: Dec. 16, 2016

(87) PCT Pub. No.: WO2016/008961

PCT Pub. Date: Jan. 21, 2016

(65) Prior Publication Data

US 2018/0214531 A1 Aug. 2, 2018

(30) Foreign Application Priority Data

Jul. 17, 2014 (EP) .................................... 14177563

(51) Int. Cl.

*A61K 39/095* (2006.01)
*C07K 14/22* (2006.01)
*A61K 39/00* (2006.01)
*A61K 39/385* (2006.01)

(52) U.S. Cl.

CPC .......... *A61K 39/095* (2013.01); *A61K 39/385* (2013.01); *C07K 14/22* (2013.01); *A61K 39/00* (2013.01); *A61K 2039/545* (2013.01); *A61K 2039/55505* (2013.01); *A61K 2039/70* (2013.01); *C07K 2319/00* (2013.01)

(58) Field of Classification Search

CPC ........ A61K 39/095; A61K 2039/55505; A61K 2039/70; A61K 2039/55583; A61K 2039/6018; A61K 47/02; A61K 38/164; A61K 39/00; A61K 2039/523; A61K 2039/545; A61K 2039/55511; A61K 2039/575; A61K 39/385; C07K 14/22; C07K 2319/00; C07K 2319/33

See application file for complete search history.

(56) References Cited

U.S. PATENT DOCUMENTS

| | | | |
|---|---|---|---|
| 10,392,424 B2 | 8/2019 | Bottomley et al. | |
| 11,021,522 B2 | 6/2021 | Bottomley et al. | |
| 11,066,450 B2 * | 7/2021 | Bottomley ........... | A61K 39/095 |
| 2007/0020624 A1 | 1/2007 | Rubenfield et al. | |
| 2007/0027309 A1 | 2/2007 | Weinstock et al. | |
| 2008/0063665 A1 * | 3/2008 | Oster ................... | A61K 39/095 424/232.1 |
| 2017/0008933 A1 | 1/2017 | Bottomley et al. | |
| 2017/0226161 A1 | 8/2017 | Bottomley et al. | |
| 2018/0214531 A1 | 8/2018 | Biolchi et al. | |
| 2021/0253647 A1 * | 8/2021 | Bottomley .............. | A61P 37/04 |

FOREIGN PATENT DOCUMENTS

| | | | |
|---|---|---|---|
| CN | 102816217 | A | 12/2012 |
| CN | 106795208 | A | 5/2017 |
| JP | 2006-521782 | A | 9/2006 |
| JP | 2017-502625 | A | 2/2015 |
| JP | 6687597 | B2 | 4/2020 |
| WO | WO 01/52885 | A1 * | 7/2001 |
| WO | 2004/048404 | A2 | 6/2004 |
| WO | 2004048404 | A2 | 6/2004 |
| WO | 2006/024954 | A2 | 3/2006 |
| WO | 2007/060548 | A2 | 5/2007 |
| WO | 2007060548 | A2 | 5/2007 |
| WO | 2008/079372 | A2 | 7/2008 |
| WO | 2011/110634 | A1 | 9/2011 |
| WO | 2011/126863 | A1 | 10/2011 |
| WO | 2013/186753 | A1 | 12/2013 |
| WO | 2014030003 | A1 | 2/2014 |
| WO | 2015/128480 | | 9/2015 |
| WO | 2016008960 | A1 | 1/2016 |

OTHER PUBLICATIONS

Skolnick et al. Trends in Biotechnology 18: 34-39, 2000.*
McGuinness et al. Lancet 337: 514-517, 1991.*
Rudinger J. In: Peptide Hormones. (Ed) JA Parsons, University Park Press, pp. 1-7, 1976.*
Lazar et al. Mol. Cellular Biol. 8: 1247-1252, 1988.*
McGuinness et al. Mol. Microbiol. 7: 505-514, 1993.*
Select prosecution papers of U.S. Appl. No. 11/066,450 B2.*
Snape et al. Pediatr. Infect. Dis. J. 29: e71-e79, 2010.*
Intellectual Property Office of Singapore, Written Opinion dated Jan. 26, 2018 for Singapore Appl. No 11201610945P (based on Int'l. Appl. No. PCT/EP2015/066229 filed Jul. 16, 2015); 8 total pages.
Esposito Susanna et al: "A phase I I randomized controlled trial of a multicomponent meningococcal serogroup B vaccine, 4CMenB, in infants (II)", Human Vaccines & Immunotherapeutics Jul. 2014, vol. 10, No. 7, Jul. 11, 2014 (Jul. 11, 2014), pp. 2005-2014.
D. M. Granoff et al: "Does Binding of Complement Factor H to the Meningococcal Vaccine Antigen, Factor H Binding Protein, Decrease Protective Serum Antibody Responses?", Clinical and Vaccine Immunology, vol. 20, No. 8, Jun. 5, 2013, pp. 1099-1107.
Peter T. Beernink et al: "The Effect of Human Factor H on Immunogenicity of Meningococcal Native Outer Membrane Vesicle Vaccines with Over-Expressed Factor H Binding Protein", PLOS Pathogens, vol. 8, No. 5, May 10, 2012, pp. e1002688-e1002688 (9 total pages).

(Continued)

*Primary Examiner* — S. Devi

(57) ABSTRACT

Meningococcal vaccines can be improved by including multiple alleles or variants of fHbp, in order to provide broader coverage of the diversity which is known for this protein, and/or by reducing the quantity of an OMV component in each dose.

4 Claims, 6 Drawing Sheets

Specification includes a Sequence Listing.

(56) References Cited

OTHER PUBLICATIONS

Koeberling Oliver et al: "Meningococcal outer membrane vesicle vaccines derived from mutant strains engineered to express factor H binding proteins from antigenic variant groups 1 and 2", Clinical and Vaccine Immunology, American Society for Microbiology, Washington, DC, US, vol. 16, No. 2, Feb. 1, 2009, pp. 156-162.
Assessment report of Bexsero (common name "Meningococcal group B Vaccine (rDNA, component, adsorbed)") by the European Medicines Agency (Committee for Medicinal Products for Human Use (CHMP)); Procedure No. EMEA/H/C/002333; dated Nov. 15, 2012, available online at http://www.ema.europa.eu/docs/en GB/document library/EPAR_-_Public_ assessment_report/human/002333/WC500137883.pdf; retrieved on Dec. 16, 2016; 102 total pages.
Dan M Granoff et al: "Chapter 21 Section: Two: Licensed vaccines—Meningococcal vaccines" in "Vaccines (6th Edition)", Jan. 1, 2013 (Jan. 1, 2013), Elsevier, XP055150061, ISBN: 978-1-45-570090-5; pp. 388-418.
International Search Report and Written Opinion for Application No. PCT/EP2015/066229 dated Jan. 10, 2015, by the European Patent Office as International Searching Authority, 15 total pages.
R. Pajon et al: "Design of Meningococcal Factor H Binding Protein Mutant Vaccines That Do Not Bind Human Complement Factor H", Infection and Immunity, vol. 80, No. 8, May 21, 2012 (May 21, 2012), pp. 2667-2677.
Muriel C Schneider et al: "Neisseria meningitidis recruits factor H using protein mimicry of host carbohydrates", Nature, Nature Publishing Group, United Kingdom, vol. 458, No. 7240, Apr. 16, 2009 (Apr. 16, 2009), pp. 890-893.
Beernink Peter T et al: "Impaired immunogenicity of a meningococcal factor H-binding protein vaccine engineered to eliminate factor h binding" Clinical and Vaccine Immunology, American Society for Microbiology, Washington, DC, US, vol. 17, No. 7, Jul. 1, 2010 (Jul. 1, 2010), pp. 1074-1078.
Rossi Raffaella et al: "Meningococca factor H-binding protein vaccines with decreased binding to human complement factor H have enhanced immunogenicity in human factor H transgenic mice", Vaccine, vol. 31, No. 46, 2013, pp. 5451-5457.
S. Van Der Veen et al: "Nonfunctional Variant 3 Factor H Binding Proteins as Meningococcal Vaccine Candidates", Infection and Immunity, vol. 82, No. 3, Dec. 30, 2013 (Dec. 30, 2013), pp. 1157-1163.
The sequence available as UniProtKB Accession No. L0GGE0, entitled Factor H binding protein, submitted Mar. 6, 2013, available at http://www.uniprot.org/uniprot/L0GGE0.txt?version=1.
The sequence available as UniProtKB Accession No. L0GFA3, entitled Factor H binding protein, submitted Mar. 6, 2013, available at http://www.uniprot.org/uniprot/L0GFA3.txt?version=1.
International Search Report and Written Opinion for Application No. PCT/EP2015/066228 dated Aug. 26, 2015, by the European Patent Office as International Searching Authority, 14 total pages.
Greenspan and Di Cera, "Defining epitopes: it's not as easy as it seems", 1999 Nature Biotechnology 17: 936-937.
Bowie et al., "Deciphering the message in protein sequences: tolerance to amino acid substitutions", 1990 Science 247(4948):1306-1310.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", 1990 J. of Cell. Bio. 111(5):2129-2138.
Lazar et al. "Transforming Growth Factor ox: Mutation of Aspartic Acid 47 and Leucine 48 Results in Different Biological Activities" 1988 Molecular and Cellular Biology 8(3):1247-1252.
Bork "Powers and Pitfalls in Sequence Analysis: the 70% hurdle", 2000 Genome Research 10(4): 398-400.
Beernink et al., Rapid Genetic Grouping of Factor H-Binding Protein (Genome-Derived Neisserial Antigen 1870), a Promising Group B Meningococcal Vaccine Candidate, 2006 Clinical and Vaccine Immunology 13(7): 758-763.
Johnson et al., Design and Evaluation of Meningococcal Vaccines through Structure-Based Modification of Host and Pathogen Molecules 2012 PLoS Pathogen 8(10):e1002981; 13 total pages.
Van Der Veen et al., Nonfunctional Variant 3 Factor H Binding Proteins as Meningococcal Vaccine Candidates, 2014 Infection and Immunity 82(3):1157-1163.
Masignani et al., Vaccination against Neisseria meningitidis Using Three Variants of the Lipoprotein GNA1870 2003 J. Exp. Med 197(6):789-799.
Beernink, et al., A meningococcal factor H binding protein mutant that eliminates factor H binding enhances protective antibody responses to vaccination, 2011 J. Immunol. 186(6):3606-3614.
Beernink, et al., "Fina Antigenic Specificity and Cooperative Bactericidal Activity of Monoclonal Antibodies Directed at the Meningococcal Vaccine Candidate for Factor H-Binding Protein" Infection and Immunity 76(9):4232-4240.
Beernink & Granoff, The modular architecture of meningococcal factor H-binding protein, 2009 Microbiology 155:2873-2883.
Brehony, et al., Variation of the factor H-binding protein of Neisseria meningitidis, 2009, Microbiology 155:4155-4169 at p. 4161.
Giuntini et al., "Monoclonal Antibodies to Meningococcal Factor H Binding Protein with Overlapping Epitopes and Discordant Functional Activity", PLOS One, vol. 7, No. 3; pp. e34272-e34272 (2012).
Jacobsson et al., "Prevalence and sequence variations of the genes encoding the five antigens included in the novel 5CVMB vaccine covering group B meningococcal disease", Vaccine, 27:10; pp. 1579-1584 (2009).
Lucidarme, J. sequence entitled "Factor H-binding protein" published as UniProtKB Accession No. D3JZH2, dated Mar. 23, 2010, available at http://www.uniprot.org/uniprot/D3JZH2.txt?version=1.
Lucidarme, J. sequence entitled "Factor H-binding protein" published as UniProtKB Accession No. D3JZI3, dated Mar. 23, 2010, available at http://www.uniprot.org/uniprot/D3JZI3.txt?version=1.
Murphy, E. sequence entitled "Factor H binding protein variant A93_001" published as UniProtKB Accession No. G9I6U8, dated Feb. 22, 2012, available at http://www.uniprot.org/uniprot/G9I6U8.txt?version= 1.
Peng Shi-ze, et al., Expression and Immunological Analysis of Recombinant Nessaria Meningitis Group B Recombinant fHBP Fusion Protein, China Biotechnology, 2010, p. 28-33, vol. 31(5) (English Language Abstract).
Romanelli, et al. sequence entitled "Factor H binding protein" published as UniProtKB Accession No. L0GFA3, dated Mar. 6, 2013, available at http://www.uniprot.org/uniprot/LOGFA3.txt?version=1.
Romanelli, et al. sequence entitled "Factor H binding protein" published as UniProtKB Accession No. L0GGE0, dated Mar. 6, 2013, available at http://www.uniprot.org/uniprot/LOGGEO.txt?version=1.
Schneider, MC, et al., Neisseria meningitidis recruits factor H using protein mimicry of host carbohydrates, 2009 Nature 458(7240): 890-893.
Zlotnick, G. W.; sequence described as "Neisseria ORF2086 subfamily A protein" corresponding to Seq ID No. 6 of international patent application publication WO2008079372; sequence published as Geneseq Accession No. ASQ06840, dated Sep. 4, 2008.
European Patent Office, office action received for corresponding EP Appl. No. 15 707 351.1 (published as EP3110442), dated Aug. 8, 2017, 5 total pages.
European Patent Office, priority search results and written opinion received for corresponding application EP 14 15 7399 (8 pages) dated Sep. 18, 2014.
European Patent Office as International Searching Authority, International Search Report and Written Opinion for International Appl. No. PCT/EP2015/054174 (published as WO 2015128480), dated Sep. 3, 2015, 11 total pages.
Mar. 10, 2016 (Mar. 10, 2016), "N. meningitidis mature truncated mutant fHbp protein S32V/L 126R, SEO 44.", retrieved from EBI accession No. GSP:BCL30499 Database accession No. BCL30499; & Database Geneseq [Online].

(56) References Cited

OTHER PUBLICATIONS

Mar. 10, 2016 (Mar. 10, 2016), "N. meningitidis mature truncated mutant fHbp protein S32V/L 123R, SEO 45.", retrieved from EBI accession No. GSP:BCL30500 Database accession No. BCL30500; & Database Geneseq [Online].

Mar. 10, 2016 (Mar. 10, 2016), "N. meningitidis M1239 mature truncated mutant fHbp protein L 126R, SEO 56.", retrieved from EBI accession No. GSP:BCL30511 Database accession No. BCL30511; & Database Geneseq [Online].

Mar. 10, 2016 (Mar. 10, 2016), "N. meningitidis 2996 mature truncated mutant fHbp protein L 123R, SEO 54.", retrieved from EBI accession No. GSP:BCL30509 Database accession No. BCL30509; & Database Geneseq [Online].

Mar. 10, 2016 (Mar. 10, 2016), "Neisseria meningitidis mutant fHbp fusion protein sequence B, SEO ID 30.", retrieved from EBI accession No. GSP:BCL30485 Database accession No. BCL30485.

European Patent Office, priority search results and written opinion received for corresponding application EP 14 17 7566 (16 pages) dated Nov. 21, 2014.

* cited by examiner

MENINGOCOCCUS VACCINES

INCORPORATION-BY-REFERENCE OF SEQUENCE LISTING OR TABLE

The content of the sequence listing (ASCII text file entitled "VN56308 WO PCT Sequence Listing.txt"; 151,764 bytes: dated Jul. 17, 2014) submitted electronically via EFS-WEB in International Application No. PCT/EP2015/066229, filed Jul. 16, 2015, is incorporated herein by reference in its entirety.

TECHNICAL FIELD

This invention is in the field of meningococcal vaccination.

BACKGROUND

*Neisseria meningitidis* is a Gram-negative encapsulated bacterium which colonises the upper respiratory tract of approximately 10% of human population. Conjugate vaccines are available against serogroups A, C, W135 and Y, but the only vaccine which is available for protecting against serogroup B in general is the BEXSERO™ product which was approved in 2013. This product includes four main immunogenic components: the factor H binding protein, 'fHbp'; the heparin binding protein, NHBA: Neisserial adhesin A, NadA; and outer membrane vesicles (OMVs).

SUMMARY OF THE INVENTION

An aspect of the present invention is an immunogenic composition comprising a fusion polypeptide comprising all three of v1, v2 and v3 meningococcal fHbp, in combination with one or more of (i) a NHBA polypeptide (ii) a NadA polypeptide and/or (iii) meningococcal outer membrane vesicles.

A further aspect of the invention is an immunogenic composition comprising meningococcal outer membrane vesicles in combination with one or more of (i) a NHBA polypeptide (ii) a NadA polypeptide and/or (iii) a fusion polypeptide comprising all three of v1, v2 and v3 meningococcal fHbp; where the outer membrane vesicles (OMVs) are present at a concentration between 5-30 μg/ml. Particularly the fusion polypeptide comprising all three of v1, v2 and v3 meningococcal fHbp is a stabilised and/or fHbp non-binding fusion polypeptide. Yet more particularly, the v1 fHbp comprises a mutation at position R41, for example an R41S mutation. Still yet more particularly, the v2 and v3 fHbp polypeptides comprise one or more stabilising and/or factor H (fH) non-binding mutations at the following positions numbered according to the full length sequences (SEQ ID NOs: 1 & 3) and also according to the ΔG sequences (SEQ ID NOs: 8 & 9):

| | | Stabilising | | fH non-binding |
|---|---|---|---|---|
| v2 | SEQ ID NO: 1 | Ser-58 | Leu-149 | Glu-266 |
| | SEQ ID NO: 8 | Ser-32 | Leu-123 | Glu-240 |
| v3 | SEQ ID NO: 3 | Ser-63 | Leu-157 | Glu-274 |
| | SEQ ID NO: 7 | Ser-32 | Leu-126 | Glu-243 |

A further aspect of the present invention is an immunogenic composition comprising a fusion polypeptide having an amino acid sequence of formula $NH_2$-A-[-X-L]$_3$-B—COOH, where each X is a different variant fHbp sequence, L is an optional linker amino acid sequence, A is an optional N terminal amino acid sequence, and B is an optional C terminal amino acid sequence.

A further aspect of the present invention is a method for protecting a mammal, such as a human, against a meningococcal infection, comprising administering an immunogenic composition according to the invention.

DETAILED DESCRIPTION

Figure 1:
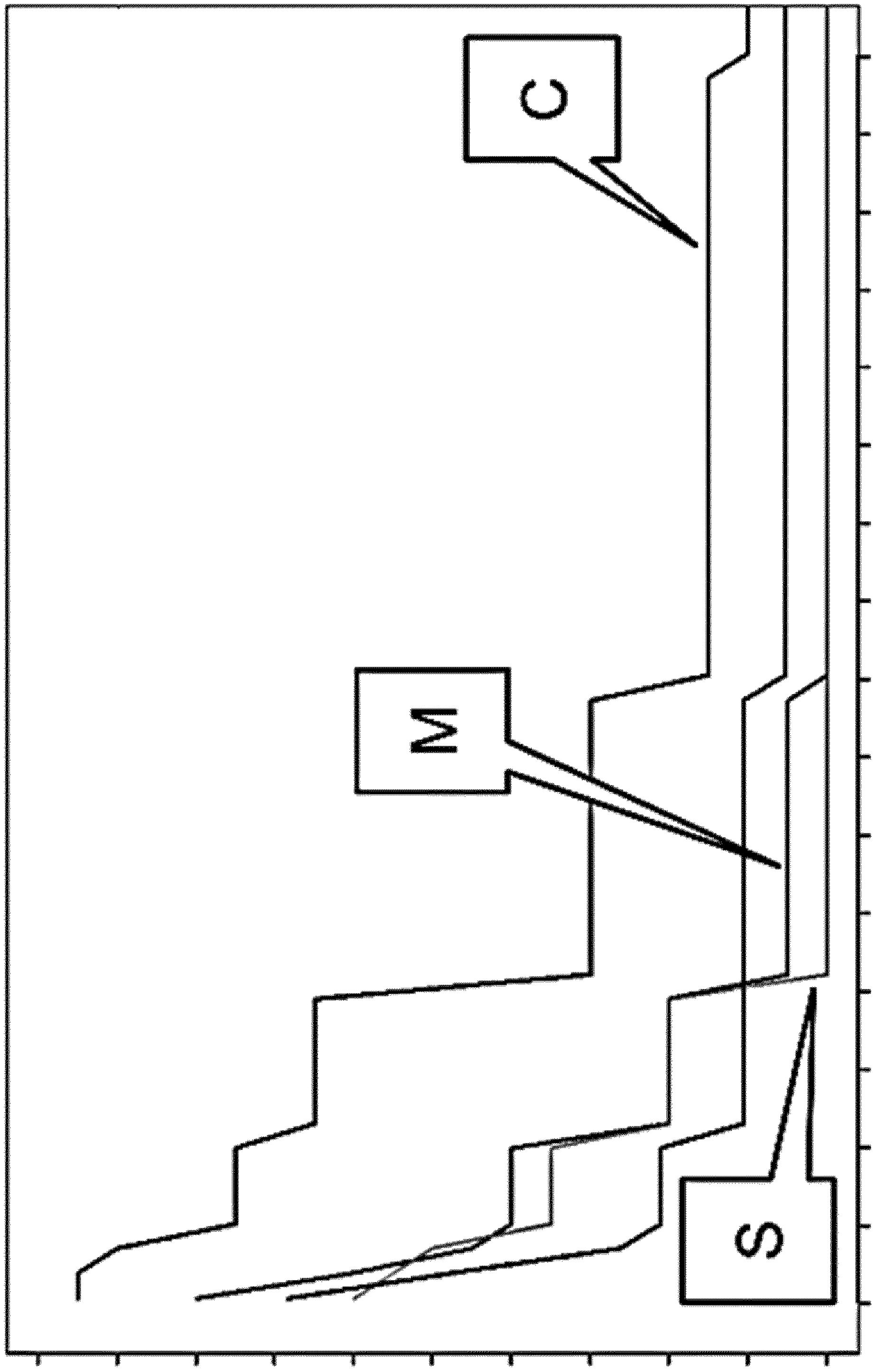
FIG. 1 shows a RCD curve, with proportion on the y-axis (0.0 to 1.0) and SBA titer on the x-axis (0 to 256, in steps of 16). The top curve is group C; the group which reaches 0.0 soonest is S.

To enhance the BEXSERO™ product it would be advantageous to further enhance the coverage of BEXSERO™ against diverse meningococcal strains (in case of potential shifts and mutations as the vaccine's use spreads) and also to reduce the rare occurrences of fever which are sometimes seen when the vaccine is co-administered with routine infant vaccines [1]. With these aims the inventors have modified BEXSERO™ in two ways: (i) to include multiple alleles or variants of fHbp, in order to provide broader coverage of the diversity which is known for this protein; and (ii) to reduce the quantity of the OMV component in each dose. As shown herein, these two modifications indeed lead to an improvement in the vaccine.

Thus, in a first embodiment the invention provides an immunogenic composition comprising a fusion polypeptide comprising all three of v1, v2 and v3 meningococcal fHbp, in combination with one or more of (i) a NHBA polypeptide (ii) a NadA polypeptide and/or (iii) meningococcal outer membrane vesicles.

Furthermore, in a second embodiment the invention provides an immunogenic composition comprising meningococcal outer membrane vesicles in combination with one or more of (i) a NHBA polypeptide (ii) a NadA polypeptide and/or (iii) a fusion polypeptide comprising all three of v1, v2 and v3 meningococcal fHbp; wherein the outer membrane vesicles are present at a concentration between 5-30 μg/ml.

Similarly, combining both of these embodiments, the invention provides an immunogenic composition comprising a (i) a fusion polypeptide comprising all three of v1, v2 and v3 meningococcal fHbp, (ii) a NHBA polypeptide (iii) a NadA polypeptide and (iv) 5-30 μg/ml meningococcal outer membrane vesicles.

Factor H Binding Protein (fHbp)

A composition of the invention may include an immunogenic fHbp polypeptide. The BEXSERO™ product includes a fHbp polypeptide, and fHbp has also been known as '741' (SEQ ID NO: 2536 in ref. 2; SEQ ID 1 herein), 'NMB1870'. 'GNA1870' [3-5], 'P2086', 'LP2086' or 'ORF2086' [6-8]. The 3D structure of this protein is known [9,10], and the protein has two β-barrels connected by a short linker. Many publications have reported on the protective efficacy of this protein in meningococcal vaccines e.g. see references 11-15. This protein is expressed in lipidated form in multiple strains across all serogroups. fHbp sequences have been grouped into three variants [3] (referred to herein as v1, v2 and v3), and it has been found in general that serum raised against a given variant is bactericidal against strains which express that variant, but is not active against strains which express one of the other two variants i.e. there is intra-variant cross-protection, but not inter-variant cross-protection (except for some v2 and v3 cross-reactivity).

To increase inter-variant cross-reactivity the fHbp sequence has been engineered to contain specificities for all three variants [16]. Instead of following this approach, however, the invention utilises a fusion polypeptide which comprises all three of v1, v2 and v3 meningococcal fHbp.

```
v1 fHbp
Full-length fHbp from strain MC58 in v1 has the
following amino acid sequence (SEQ ID NO: 1):
MNRTAFCCLSLTTALILTACSSGGGGVAADIGAGLADALTAPLDHKDKGL

QSLTLDQSVRKNEKLKLAAQGAEKTYGNGDSLNTGKLKNDKVSREDFIRQ

IEVDGQLITLESGEFQVYKQSHSALTAFQTEQIQDSEHSGKMVAKRQFRI

GDIAGEHTSFDKLPEGGRATYRGTAFGSDDAGGKLTYTIDFAAKQGNGKI

EHLKSPELNVDLAAADIKPDGKRHAVISGSVLYNQAEKGSYSLGIEGGKA

QEVAGSAEVKTVNGIRHIGLAAKQ
```

The mature lipoprotein lacks the first 19 amino acids of SEQ ID NO: 1 (underlined; provides SEQ ID NO: 4, beginning with Cys-20). The BEXSERO™ product includes a 'ΔG' form of v1 fHbp in which the full-length sequence is truncated up to residue 26 (i.e. to remove the poly-glycine stretch beginning instead with Val-27), giving SEQ ID NO: 7.

A v1 meningococcal fHbp used with the invention will comprise an amino acid sequence (i) with at least i % sequence identity to SEQ ID NO: 7, and/or (ii) comprising a fragment of SEQ ID NO: 7.

The value of i may be selected from 80, 85, 86, 87, 88, 89, 90, 91, 92, 93, 94, 95, 96, 97, 98, 99 or more. It is preferably 90 (i.e. the amino acid sequence has at least 90% identity to SEQ ID NO: 7) and is more preferably 95.

The fragment of (ii) will generally be at least 7 amino acids long e.g. 8, 10, 12, 14, 16, 18, 20, 22, 24, 26, 28, 30, 32, 24, 26, 28, 40, 45, 50, 55, 60, 65, 70, 75, 80 or more contiguous amino acids from SEQ ID NO: 7. The fragment will typically include at least one epitope from SEQ ID NO: 7. Epitope identification and mapping is established for fHbp [12; 17-21]. Sharing at least 30 contiguous amino acids with SEQ ID NO: 7 will be typical, and usually a v1 fHbp amino acid sequence will include several (e.g. 2, 3, 4, 5 or more) fragments from SEQ ID NO: 7.

Overall, a v1 fHbp amino acid sequence can have at least i % sequence identity to and include several fragments of SEQ ID NO: 7.

A v1 fHbp sequence generally includes at least one amino acid sequence which is not present in SEQ ID NO: 2 and/or at least one amino acid sequence which is not present in SEQ ID NO: 3.

A polypeptide used with the invention and including a v1 sequence can, after administration to a suitable host mammal (such as a mouse or a human), elicit antibodies which can recognise a wild-type meningococcal polypeptide consisting of SEQ ID NO: 4. These antibodies will include some antibodies which do not recognise a v2 or a v3 polypeptide (e.g. will not recognise a wild-type meningococcal polypeptide consisting of SEQ ID NO: 5 and a wild-type meningococcal polypeptide consisting of SEQ ID NO: 6), although they may also include some antibodies which cross-react with v2 and/or v3 polypeptides. The antibodies are ideally bactericidal against a meningococcal strain which expresses a v1 fHbp e.g. against the MC58 strain (see below).

```
v2 fHbp
Full-length fHbp from strain 2996 in v2 has the
following amino acid sequence (SEQ ID NO: 2):
MNRTAFCCLSLTAALILTACSSGGGGVAADIGAGLADALTAPLDHKDKSL

QSLILDQSVRKNEKLKLAAQGAEKTYGNGDSLNIGKLKNDKVSREDFIRQ

IEVDGQLITLESGEFQIYKQDHSAVVALQIEKINNPDKIDSLINQRSELV

SGLGGEHTAFNQLPDGKAEYHGKAFSSDDAGGKLTYTIDFAAKQGHGKIE

HLKTPEQNVELAAAELKADEKSHAVILGDTRYGSEEKGTYHLALFGDRAQ

EIAGSATVKIGEKVHEIGIAGKQ
```

The mature lipoprotein lacks the first 19 amino acids of SEQ ID NO: 2 (underlined; provides SEQ ID NO: 5), and the ΔG form of SEQ ID NO: 2 lacks the first 26 amino acids (SEQ ID NO: 8).

A v2 meningococcal fHbp used with the invention will comprise an amino acid sequence (i) with at least j % sequence identity to SEQ ID NO: 8, and/or (ii) comprising a fragment of SEQ ID NO: 8.

The value of j may be selected from 80, 85, 86, 87, 88, 89, 90, 91, 92, 93, 94, 95, 96, 97, 98, 99 or more. It is preferably 90 (i.e. the amino acid sequence has at least 90% identity to SEQ ID NO: 8) and is more preferably 95.

The fragment of (ii) will generally be at least 7 amino acids long e.g. 8, 10, 12, 14, 16, 18, 20, 22, 24, 26, 28, 30, 32, 24, 26, 28, 40, 45, 50, 55, 60, 65, 70, 75, 80 or more contiguous amino acids from SEQ ID NO: 8. The fragment will typically include at least one epitope from SEQ ID NO: 8. Epitope identification and mapping is established for fHbp (see above). Sharing at least 30 contiguous amino acids with SEQ ID NO: 8 will be typical, and usually a v2 fHbp amino acid sequence will include several (e.g. 2, 3, 4, 5 or more) fragments from SEQ ID NO: 8.

Overall, a v2 fHbp amino acid sequence can have at least j % sequence identity to and include several fragments of SEQ ID NO: 8.

A v2 fHbp sequence generally includes at least one amino acid sequence which is not present in SEQ ID NO: 1 and/or at least one amino acid sequence which is not present in SEQ ID NO: 3.

A polypeptide used with the invention and including a v2 sequence can, after administration to a suitable host mammal (such as a mouse or a human), elicit antibodies which can recognise a wild-type meningococcal polypeptide consisting of SEQ ID NO: 5. These antibodies will include some antibodies which do not recognise a v1 or a v3 polypeptide (e.g. will not recognise a wild-type meningococcal polypeptide consisting of SEQ ID NO: 4 and a wild-type meningococcal polypeptide consisting of SEQ ID NO: 6), although they may also include some antibodies which cross-react with v1 and/or v3 polypeptides. The antibodies are ideally bactericidal against a meningococcal strain which expresses a v2 fHbp e.g. against the M2091 strain (see below).

```
v3 fHbp
Full-length fHbp from strain M1239 in v3 has the
following amino acid sequence (SEQ ID NO: 3):
MNRTAFCCLSLTTALILTACSSGGGGSGGGGVAADIGTGLADALTAPLDH

KDKGLKSLTLEDSIPQNGTLTLSAQGAEKTFKAGDKDNSLNTGKLKNDKI

SREDEVQKIEVDGQTITLASGEFQTYKQNHSAVVALQIEKINNPDKTDSL

INQRSELVSGLGGEHTAFNQLPGGKAEYHGKAFSSDDPNGRLHYSIDETK

KQGYGRIEHLKTLEQNVELAAAELKADEKSHAVILGDTRYGSEEKGTYHL

ALFGDRAQEIAGSATVKIGEKVHEIGIAGKQ
```

The mature lipoprotein lacks the first 19 amino acids of SEQ ID NO: 3 (underlined; provides SEQ ID NO: 6), and the ΔG form of SEQ ID NO: 3 lacks the first 31 amino acids (SEQ ID NO: 9).

A v3 meningococcal fHbp used with the invention will comprise an amino acid sequence (i) with at least k % sequence identity to SEQ ID NO: 9, and/or (ii) comprising a fragment of SEQ ID NO: 9.

The value of k may be selected from 80, 85, 86, 87, 88, 89, 90, 91, 92, 93, 94, 95, 96, 97, 98, 99 or more. It is preferably 90 (i.e. the amino acid sequence has at least 90% identity to SEQ ID NO: 9) and is more preferably 95.

The fragment of (ii) will generally be at least 7 amino acids long e.g. 8, 10, 12, 14, 16, 18, 20, 22, 24, 26, 28, 30, 32, 24, 26, 28, 40, 45, 50, 55, 60, 65, 70, 75, 80 or more contiguous amino acids from SEQ ID NO: 9. The fragment will typically include at least one epitope from SEQ ID NO: 9. Epitope identification and mapping is established for fHbp (see above). Sharing at least 30 contiguous amino acids with SEQ ID NO: 9 will be typical, and usually a v3 fHbp amino acid sequence will include several (e.g. 2, 3, 4, 5 or more) fragments from SEQ ID NO: 9.

Overall, a v3 fHbp amino acid sequence can have at least k % sequence identity to and include several fragments of SEQ ID NO: 9.

A v3 fHbp sequence generally includes at least one amino acid sequence which is not present in SEQ ID NO: 1 and/or at least one amino acid sequence which is not present in SEQ ID NO: 2.

A polypeptide used with the invention and including a v3 sequence can, after administration to a suitable host mammal (such as a mouse or a human), elicit antibodies which can recognise a wild-type meningococcal polypeptide consisting of SEQ ID NO: 6. These antibodies will include some antibodies which do not recognise a v1 or a v2 polypeptide (e.g. will not recognise a wild-type meningococcal polypeptide consisting of SEQ ID NO: 4 and a wild-type meningococcal polypeptide consisting of SEQ ID NO: 5), although they may also include some antibodies which cross-react with v1 and/or v2 polypeptides. The antibodies are ideally bactericidal against a meningococcal strain which expresses a v3 fHbp e.g. against the M01-240355 strain (see below).

Fusion Polypeptide

The invention utilises a fusion polypeptide which comprises all three of v1, v2 and v3 meningococcal fHbp. As a result, the fusion polypeptide can include at least one epitope from each of SEQ ID NOs: 7, 8, and 9 and, after administration to a host mammal, can elicit antibodies which can recognise all three of (i) a wild-type meningococcal polypeptide consisting of SEQ ID NO: 4, (ii) a wild-type meningococcal polypeptide consisting of SEQ ID NO: 5, and (iii) a wild-type meningococcal polypeptide consisting of SEQ ID NO: 6. These antibodies are ideally bactericidal against a meningococcal strain which expresses a v1 fHbp, a meningococcal strain which expresses a v2 fHbp, and also a meningococcal strain which expresses a v3 fHbp (e.g. against each of the MC58, M2091, and M01-240355 strains).

With reference to the definitions given above, where relevant, for the fusion polypeptide it is preferred that i=j=k.

In general a fHbp fusion polypeptide of the invention has an amino acid sequence of formula:

$$NH_2\text{-A-[-X-L-]}_3\text{-B—COOH}$$

wherein each X is a different variant fHbp sequence, L is an optional linker amino acid sequence, A is an optional N-terminal amino acid sequence, and B is an optional C-terminal amino acid sequence.

The three X moieties are a v1, v2, and v3 sequence as discussed above. These can be present in any order from N- to C-terminus i.e. v1-v2-v3, v1-v3-v2, v2-v1-v3, v2-v3-v1, v3-v1-v2, or v3-v2-v1.

The most preferred order is v2-v3-v1.

For each instance of [-X-L-], linker amino acid sequence -L- may be present or absent. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. Gly, where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. One useful linker is GSGGGG (SEQ ID NO: 22), with the Gly-Ser dipeptide being formed from a BamHI restriction site, thus aiding cloning and manipulation. Another useful linker is SEQ ID NO: 23, which can optionally be preceded by a Gly-Ser dipeptide (SEQ ID NO: 24, from BamHI) or a Gly-Lys dipeptide (SEQ ID NO: 25, from HindIII).

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking. If $X_1$ lacks its own N-terminus methionine, -A- may provide such a methionine residue in the translated polypeptide (e.g. -A- is a single Met residue). The Met may be to the N-terminus of a linker sequence such as SEQ ID NO: 23 (i.e. SEQ ID: 26), or at the N-terminus of a short sequence (e.g. SEQ ID NO: 27).

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance polypeptide stability. Other suitable C-terminal amino acid sequences will be apparent to those skilled in the art. One suitable -B- moiety is SEQ ID NO: 28, in which the Leu-Glu upstream of the histidine tag arises from a XhoI restriction site.

One fusion polypeptide suitable for use with the invention comprises SEQ ID NO: 10. According to the above formula, in SEQ ID NO: 10 -A- is SEQ ID NO: 26, $X_1$ is a v2 fHbp sequence (SEQ ID NO: 8), $-L_1-$ is SEQ ID NO: 24, $X_2$ is a v3 fHbp sequence (SEQ ID NO: 9), $-L_2-$ is SEQ ID NO: 22, $X_3$ is a v1 fHbp sequence (SEQ ID NO: 7), and $L_3$ and B are absent. The three fHbp sequences in SEQ ID NO: 10 are underlined below:

```
MGPDSDRLQQRRVAADIGAGLADALTAPLDHKDKSLQSLTLDQSVRKNE
KLKLAAQGAEKTYGNGDSLNTGKLKNDKVSRFDFIRQIEVDGQLITLES
GEFQIYKQDHSAVVALQIEKINNPDKIDSLINQRSFLVSGLGGEHTAFN
QLPDGKAEYHGKAFSSDDAGGKLTYTIDFAAKQGHGKIEHLKTPEQNVE
LAAAELKADEKSHAVILGDTRYGSEEKGTYHLALFGDRAQEIAGSATVK
IGEKVHEIGIAGKQGSGPDSDRLQQRRVAADIGTGLADALTAPLDHKDK
GLKSLTLEDSIPQNGTLTLSAQGAEKTFKAGDKDNSLNTGKLKNDKISR
FDFVQKIEVDGQTITLASGEFQIYKQNHSAVVALQIEKINNPDKTDSLI
NQRSFLVSGLGGEHTAFNQLPGGKAEYHGKAFSSDDPNGRLHYSIDFTK
KQGYGRIEHLKTLEQNVELAAAELKADEKSHAVILGDTRYGSEEKGTYH
LALFGDRAQEIAGSATVKIGEKVHEIGIAGKQGSGGGGVAADIGAGLAD
ALTAPLDHKDKGLQSLTLDQSVRKNEKLKLAAQGAEKTYGNGDSLNTGK
LKNDKVSRFDFIRQIEVDGQLITLESGEFQVYKQSHSALTAFQTEQIQD
SEHSGKMVAKRQFRIGDIAGEHTSFDKLPEGGRATYRGTAFGSDDAGGK
LTYTIDFAAKQGNGKIEHLKSPELNVDLAAADIKPDGKRHAVISGSVLY
NQAEKGSYSLGIFGGKAQEVAGSAEVKTVNGIRHIGLAAKQ
```

A more preferred fusion polypeptide for use with the invention comprises SEQ ID NO: 29. According to the above formula, in SEQ ID NO: 29 -A- is SEQ ID NO: 26, $X_1$ is a v2 fHbp sequence (SEQ ID NO: 8), $L_1$ is SEQ ID NO: 22, $X_2$ is a v3 fHbp sequence (SEQ ID NO: 9), -$L_2$- is SEQ ID NO: 22, $X_3$ is a v1 fHbp sequence (SEQ ID NO: 7), and $L_3$ and B are absent. The three fHbp sequences in SEQ ID NO: 29 are underlined below:

```
MGPDSDRLQQRRVAADIGAGLADALTAPLDHKDKSLQSLTLDQSVRKNE
LAKLKAQGAEKTYGNGDSLNTGKLKNDKVSRFDFIRQIEVDGQLITLES
GEFQIYKQDHSAVVALQIEKINNPDKIDSLINQRSFLVSGLGGEHTAFN
QLPDGKAEYHGKAFSSDDAGGKLTYTIDFAAKQGHGKIEHLKTPEQNVE
LAAAELKADEKSHAVILGDTRYGSEEKGTYHLALFGDRAQEIAGSATVK
IGEKVHEIGIAGKQGSGGGGVAADIGTGLADALTAPLDHKDKGLKSLTL
EDSIPQNGTLTLSAQGAEKTFKAGDKDNSLNTGKLKNDKISRFDFVQKI
EVDGQTITLASGEFQIYKQNHSAVVALQIEKINNPDKTDSLINQRSFLV
SGLGGEHTAFNQLPGGKAEYHGKAFSSDDPNGRLHYSIDFTKKQGYGRI
EHLKTLEQNVELAAAELKADEKSHAVILGDTRYGSEEKGTYHLALFGDR
AQEIAGSATVKIGEKVHEIGIAGKQGSGGGGVAADIGAGLADALTAPLD
HKDKGLQSLTLDQSVRKNEKLKLAAQGAEKTYGNGDSLNTGKLKNDKVS
RFDFIRQIEVDGQLITLESGEFQVYKQSHSALTAFQTEQIQDSEHSGKM
VAKRQFRIGDIAGEHTSFDKLPEGGRATYRGTAFGSDDAGGKLTYTIDF
AAKQGNGKIEHLKSPELNVDLAAADIKPDGKRHAVISGSVLYNQAEKGS
YSLGIFGGKAQEVAGSAEVKTVNGIRHIGLAAKQ
```

Thus the invention ideally utilises a polypeptide having amino acid sequence SEQ ID NO: 10 or SEQ ID NO: 29, but the invention can also use a polypeptide comprising SEQ ID NO: 10 or SEQ ID NO: 29, but modified by up to 10 single amino acid changes (i.e. 1, 2, 3, 4, 5, 6, 7, 8, 9, or 10 single amino acid substitutions, deletions and/or insertions), provided that the polypeptide can elicit antibodies which can recognise all three of a wild-type meningococcal polypeptides of SEQ ID NOs: 4-6, as discussed above. Furthermore. SEQ ID NO: 10 or SEQ ID NO: 29 can be modified to change their -A- moiety (e.g. to use an alternative to SEQ ID NO: 26), so a polypeptide used with the invention can comprise SEQ ID NO: 30, optionally modified by up to 10 single amino acid changes (as discussed above).

For instance, SEQ ID NO: 30 can be modified to introduce point mutations which disrupt the ability of each fHbp to interact with fH. For example, SEQ ID NO: 30 can be mutated at residues E240, E496, and R543, thereby giving SEQ ID NO: 31 (comprising mutations E240X, E496X and R543X, where X is any amino acid other than the recited amino acid, i.e., E240X refers to any amino acid other than E at residue 240). A preferred embodiment of SEQ ID NO: 31 is SEQ ID NO: 32 (comprising the mutations E240A, E496A, R543S). The invention can use SEQ ID NO: 31 (e.g. SEQ ID NO: 32), optionally modified by up to 5 single amino acid changes (as discussed above), provided that residues E240, E496, and R543 are not present.

Furthermore. SEQ ID NO: 30 can be modified to introduce point mutations which increase the stability of a fHbp. For example, SEQ ID NO: 30 can be mutated at residues S32, L123, S285, and L379, thereby giving SEQ ID NO: 33 (comprising mutations S32X, L123X, S285X and L379X). A preferred embodiment of SEQ ID NO: 33 is SEQ ID NO: 34 (comprising mutations S32V, L123R, S285V, L379R). The invention can use SEQ ID NO: 33 (e.g. SEQ ID NO: 34), optionally modified by up to 5 single amino acid changes (as discussed above), provided that residues S32, L123, S285, and L379 are not present. One such polypeptide is SEQ ID NO: 35, in which the v1 sequence has been modified to include a mutation as reported in ref. 22 e.g. the 'R41S' mutation (SEQ ID NO: 36). SEQ ID NO:35 comprises mutations S32X, L123X, S285X, L379X and R543X, and SEQ ID NO:36 comprises mutations S32V, L123R, S285V, L379R and R543S. The 'R41S' nomenclature is numbered relative to the mature v1 polypeptide (SEQ ID N0:4), thus, e.g., it is present in the SEQ ID NO:35 fusion polypeptide as R543X and in SEQ ID NO:36 as R543S.

These various approaches can be combined, so the invention can utilise a polypeptide comprising SEQ ID NO: 37 (e.g. a polypeptide having amino acid sequence SEQ ID NO: 38). SEQ ID NO: 37 and SEQ ID NO: 38 comprise mutations S32V, L123R, E240A, S285V, L379R. E496A and R543S.

SEQ ID NO:38 further comprises SEQ ID NO:26 at the N-terminal In a further embodiment, the invention can use SEQ ID NO: 39 (comprising mutations L123X and L379X) e.g. SEQ ID NO: 40 (comprising mutations L123R and L379R). The invention can similarly use SEQ ID NO: 39 (e.g. SEQ ID NO: 40), optionally modified by up to 5 single amino acid changes (as discussed above), provided that residues L123 and L379 are not present (e.g. see SEQ ID NO: 34, which differs from SEQ ID NO: 40 by including two SN substitutions as noted above). One such polypeptide is SEQ ID NO: 41, in which the v1 sequence has been modified to include the 'R41S' mutation, and thus comprises L123R, L379R and R543S. In further embodiments, when such fusion proteins are present in compositions of the invention, OMVs may be present at concentrations of between 2.5 μg/ml and 12.5 μg/ml.

The amino acid residues noted for mutation above are defined relative to specific starting sequences. The corresponding amino acid residues in any other fHbp sequence can be readily identified by sequence alignment e.g. being the amino acid which, when aligned using a pairwise alignment algorithm (e.g. the Needleman-Wunsch global alignment algorithm, as detailed below), aligns with the amino acid mentioned herein. Often the amino acid will be the same, but the alignment will easily identify if this is not the case.

The fHbp is naturally a lipoprotein in *N. meningitidis*. It has also been found to be lipidated when expressed in *E. coli* with its native leader sequence or with heterologous leader sequences.

Polypeptides of the invention may have a N-terminus cysteine residue, which may be lipidated e.g. comprising a palmitoyl group, usually forming tripalmitoyl-S-glyceryl-cysteine. In usual embodiments, however, the fusion polypeptide of the invention is not lipidated (typically because the N-terminal -A- moiety does not direct lipidation) in the expression host.

Neisserial Heparin Binding Antigen (NHBA)

A composition of the invention may include an immunogenic NHBA polypeptide. The NHBA antigen was included in the published genome sequence for meningococcal serogroup B strain MC58 [23] as gene NMB2132 (GenBank accession number GI:7227388; SEQ ID NO: 11 herein). The sequences of NHBA antigen from many strains have been published since then. For example, allelic forms of NHBA can be seen in FIGS. 5 and 15 of reference 24, and in example 13 and FIG. 21 of reference 2 (SEQ IDs 3179 to 3184 therein). Various immunogenic fragments of the NHBA antigen have also been reported, including the 'ΔG' fragment of SEQ ID NO: 12. Preferred NHBA antigens for use with the invention comprise an amino acid sequence: (a) having 60% or more identity (e.g. 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12.

The most useful NHBA antigens of the invention can elicit antibodies which, after administration to a suitable host mammal (such as a mouse or a human), can bind to a meningococcal polypeptide consisting of amino acid sequence SEQ ID NO: 13. Advantageous NHBA antigens for use with the invention can elicit bactericidal anti-meningococcal antibodies after administration to a mammalian subject.

A particularly preferred NHBA polypeptide for use with the invention comprises SEQ ID NO: 12, optionally modified by up to 3 single amino acid changes (i.e. 1, 2, or 3 single amino acid substitutions, deletions and/or insertions), provided that the polypeptide can elicit antibodies which can bind to SEQ ID NO: 13, as discussed above.

As seen in the BEXSERO™ product, the NHBA polypeptide can usefully be present as a fusion polypeptide e.g. fused to a NMB1030 polypeptide. In such fusion polypeptides NMB1030 is preferably downstream of NHBA. NMB1030 from strain MC58 has GenBank accession number GI:7226269 (SEQ ID NO: 14 herein). A NMB1030 sequence for use with the invention can comprise an amino acid sequence: (a) having 60% or more identity (e.g. 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 30 or more. One useful NMB1030 fragment is SEQ ID NO: 15.

One such NHBA-NMB1030 fusion polypeptide has amino acid sequence SEQ ID NO: 16. Thus the invention can use SEQ ID NO: 16, optionally modified by up to 3 single amino acid changes (i.e. 1, 2, or 3 single amino acid substitutions, deletions and/or insertions), provided that the polypeptide can elicit antibodies which can bind to SEQ ID NO: 13, as discussed above.

Neisserial Adhesin A (NadA)

A composition of the invention may include an immunogenic NadA polypeptide. The NadA antigen was included in the published genome sequence for meningococcal serogroup B strain MC58 [23] as gene NMB1994 (GenBank accession number GI:7227256: SEQ ID NO: 17 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 60% or more identity (e.g. 65%, 70%, 75%, 80%, 85%, 90%, 91%, 92%, 93%, 94%, 95%, 96%, 97%, 98%, 99%, 99.5% or more) to SEQ ID NO: 17: and/or (b) comprising a fragment of at least 'n' consecutive amino acids of SEQ ID NO: 17, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 17.

The most useful NadA antigens of the invention can elicit antibodies which, after administration to a host mammal, can bind to a meningococcal polypeptide consisting of amino acid sequence SEQ ID NO: 18. Advantageous NadA antigens for use with the invention can elicit bactericidal anti-meningococcal antibodies after administration to a host mammal.

A particularly preferred NadA polypeptide for use with the invention has SEQ ID NO: 19, optionally modified by up to 3 single amino acid changes (i.e. 1, 2, or 3 single amino acid substitutions, deletions and/or insertions), provided that the polypeptide can elicit antibodies which can bind to SEQ ID NO: 18, as discussed above.

Meningococcal Outer Membrane Vesicles (OMVs)

Compositions of the invention include meningococcal OMVs i.e. any proteoliposomic vesicle obtained by disruption of or blebbing from a meningococcal outer membrane to form vesicles therefrom that retain protein components of the outer membrane (e.g. PorA, PorB, RmpM, Opa, Opc, Omp85, FetA/FrpB, NspA, etc.), having a diameter in the range of 50-200 nm. Thus the term can include OMVs (sometimes referred to as 'blebs') as well as the vesicles referred to as microvesicles (MVs [25]) or 'native OMVs' ('NOMVs' [26]). See also references 27 to 33. Typical outer membrane vesicles are prepared artificially from bacteria, and may be prepared using detergent treatment (e.g. with deoxycholate), or by non-detergent means (e.g. see reference 37). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [34 & 35] being preferred for treating *Neisseria*) at a pH sufficiently high not to precipitate the detergent [36]. Other techniques may be performed substantially in the absence of detergent [37,38] using techniques such as sonication, homogenisation, microfluidisation, cavitation, osmotic shock, grinding, French press, blending, etc. Methods using no or low detergent can retain useful antigens such as NspA and fHbp [37]. Thus OMVs used with the invention may be prepared using an OMV extraction buffer having about 0.5% deoxycholate or lower e.g. about 0.2%, about 0.1%, <0.05% or even zero.

The vesicles known as MVs and NOMVs are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 45 & 46 describe *Neisseria* with high MV production.

Vesicles may be prepared from bacteria which have been genetically manipulated [39-42] e.g. to increase immunogenicity (e.g. hyper-express immunogens), to reduce toxicity, to inhibit capsular polysaccharide synthesis, to down-regulate PorA expression, etc. They may be prepared from hyperblebbing strains 143461. Vesicles from bacteria with different class I outer membrane protein subtypes may be used e.g. six different subtypes [47,48] using two different genetically-engineered vesicle populations each displaying three subtypes, or nine different subtypes using three different genetically-engineered vesicle populations each displaying three subtypes, etc. Useful subtypes include: P1.7,16; P1.5-1,2-2; P1.19,15-1; P1.5-2,10; P1.12-1,13; P1.7-2,4; P1.22,14; P1.7-1,1; P1.18-1,3,6. In general, however, it is preferred for the present invention to prepare OMVs from a wild-type meningococcus strain.

Vesicles for use with the invention can thus be prepared from any wild-type meningococcal strain. The vesicles will usually be from a serogroup B strain, but it is possible to prepare them from serogroups other than B (e.g. reference 36 discloses a process for serogroup A), such as A, C, W135 or Y. The strain may be of any serotype (e.g. 1, 2a, 2b, 4, 14, 15, 16, etc.), any serosubtype (e.g. P1.4), and any immunotype (e.g. L1; L2; L3: L3,7; L3,7,9; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. Most preferably, OMVs are prepared from the strain NZ98/254, or another strain with the P1.4 PorA serosubtype. The invention advantageously uses the same OMVs which are used in the BEXSERO™ and MENZB™ products, prepared from the strain NZ98/254.

Vesicles will generally include meningococcal LOS (also known as LPS), but the pyrogenic effect of LOS in OMVs is much lower than seen with the same amount of purified LOS, and adsorption of OMVs to aluminium hydroxide further reduces pyrogenicity. LOS levels are expressed in International Units (IU) of endotoxin and can be tested by the LAL assay (limulus amebocyte lysate). Preferably, LOS is present at less than 2000 IU per µg of OMV protein.

When LOS is present in a vesicle it is possible to treat the vesicle so as to link its LOS and protein components ("intra-bleb" conjugation [49]).

A useful process for OMV purification is described in reference 50 and involves ultrafiltration on crude OMVs, rather than instead of high speed centrifugation. The process may involve a step of ultracentrifugation after the ultrafiltration takes place. OMVs can also be purified using the two stage size filtration process described in ref. 51.

OMVs can usefully be suspended in a sucrose solution after they have been prepared.

Combinations

A composition of the invention can include each of (a) a fusion polypeptide comprising all three of v1, v2 and v3 meningococcal fHbp (b) a NHBA polypeptide (c) a NadA polypeptide and (d) OMVs.

In such combinations: (a) the fHbp fusion polypeptide ideally comprises amino acid sequence SEQ ID NO: 10, but optionally modified by up to 10 single amino acid changes, as discussed above; (b) the NHBA polypeptide ideally comprises amino acid sequence SEQ ID NO: 12, but optionally modified by up to 3 single amino acid changes, as discussed above; and (c) the NadA polypeptide ideally comprises amino acid sequence SEQ ID NO: 19, but optionally modified by up to 3 single amino acid changes, as discussed above.

More preferably: (a) the fHbp fusion polypeptide has amino acid sequence SEQ ID NO: 10; (b) the NHBA polypeptide comprises amino acid sequence SEQ ID NO: 12; and (c) the NadA polypeptide has amino acid sequence SEQ ID NO: 19.

Even more preferably: (a) the fHbp fusion polypeptide has amino acid sequence SEQ ID NO: 10; (b) the NHBA polypeptide has amino acid sequence SEQ ID NO: 16; and (c) the NadA polypeptide has amino acid sequence SEQ ID NO: 19.

The polypeptides in compositions of the invention can be present at any concentration which results in an effective immunological response in a host. This dosing can be established through routine testing, particularly in view of the guidance provided by the BEXSERO™ product, which has fHbp, NHBA and NadA polypeptides each present at 100 µg/ml. Thus fHbp, NHBA and/or NadA polypeptides may each be present in a composition of the invention at a concentration of between 20 µg/ml and 400 µg/ml e.g. between 50-150 µg/ml, between 80-120 µg/ml, or about 100 µg/ml. Antigen concentrations are easily quantified by standard protein assays.

Similarly, OMVs in compositions of the invention can be present at any concentration which results in an effective immunological response in a host. This dosing can be established through routine testing, particularly in view of the guidance provided by the BEXSERO™ product, in which OMVs are present at 50 µg/ml. Thus, according to the first embodiment of the invention, OMVs may be present in a composition at a concentration of between 20 µg/ml and 100 µg/ml e.g. between 30-75 µg/ml, between 40-60 µg/ml, or ideally about 50 µg/ml. In the second embodiment of the invention, however, OMVs are present at a lower concentration, namely between 5 µg/ml and 30 µg/ml e.g. between 10 µg/ml and 15 µg/ml, or ideally about 12.5 µg/ml. In certain embodiments. OMVs are present at lower concentrations of between 2.5 µg/ml and 12.5 µg/ml, for example at 2.5 µg/ml, 3.0 µg/ml, 3.5 µg/ml, 4.0 µg/ml, 4.5 µg/ml, 5.0 µg/ml, 5.5 µg/ml, 6.0 µg/ml, 6.5 µg/ml, 7.0 µg/ml, 7.5 µg/ml, 8.0 µg/ml, 8.5 µg/ml, 9.0 µg/ml, 9.5 µg/ml and 10 µg/ml.

OMV quantities and concentrations in compositions of the invention are defined in the same manner as in the BEXSERO™ product, namely by reference to their total protein content. This can be assessed using various assays e.g. ref.29 discloses use of the Folin-Lowry assay. Total protein can be assayed according to the European Pharmacopoeia, Ph. Eur. Assay 2.5.33, using any of the seven pharmacopoeial methods. Method 2 provides the Lowry test, which is preferred. Thus a composition of the second embodiment of the invention includes OMVs with 5-30 μg/ml total protein.

Polypeptides

Polypeptides of the invention can be prepared by various means e.g. by chemical synthesis (at least in part), by digesting longer polypeptides using proteases, by translation from RNA, by purification from cell culture (e.g. from recombinant expression or from *N. meningitidis* culture), etc. Heterologous expression in an *E. coli* host is a preferred expression route.

Polypeptides of the invention are ideally at least 100 amino acids long e.g. 150aa, 175aa, 200aa, 225aa, or longer. For instance, a fHbp fusion polypeptide will usually be at least 500aa long, a NHBA polypeptide will usually be at least 400aa long, and a NadA polypeptide will usually be at least 250aa long.

Polypeptides are preferably prepared in substantially pure or substantially isolated form (i.e. substantially free from other Neisserial or host cell polypeptides). In general, the polypeptides are provided in a non-naturally occurring environment e.g. they are separated from their naturally-occurring environment. In certain embodiments, the polypeptide is present in a composition that is enriched for the polypeptide as compared to a starting material. Thus purified polypeptide is provided, whereby purified means that the polypeptide is present in a composition that is substantially free of other expressed polypeptides, whereby substantially free is meant that more than 50% (e.g. ≥75%, ≥80%, ≥90%, ≥95%, or ≥99%) of total polypeptide in the composition is a polypeptide of the invention.

Polypeptides can take various forms (e.g. native, fusions, non-glycosylated, lipidated, disulfide bridges, etc.).

Sequences such as SEQ ID NO: 19 do not include a N-terminus methionine. If a polypeptide of the invention is produced by translation in a biological host then a start codon is required, which will provide a N-terminus methionine in most hosts. Thus a polypeptide of the invention will, at least at a nascent stage, include a methionine residue upstream of said SEQ ID NO sequence.

In some embodiments a polypeptide in a composition of the invention can include a N-terminal sequence upstream of (as appropriate) the fHbp, NHBA or NadA polypeptide sequence. In some embodiments the polypeptide has a single methionine at the N-terminus immediately followed by the relevant immunogen's amino acid sequence: in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. a histidine tag i.e. $His_n$ where n=4, 5, 6, 7, 8, 9, 10 or more).

A polypeptide of the invention may also include amino acids downstream of the final amino acid of the fHbp. NHBA or NadA (as appropriate) amino acid sequence. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising a histidine tag i.e. $His_n$ where n=4, 5, 6, 7, 8, 9, 10 or more), or sequences which enhance polypeptide stability. Other suitable C-terminal amino acid sequences will be apparent to those skilled in the art.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention: for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Polypeptides of the invention are preferably expressed recombinantly in a heterologous host (for example, in *E. coli*), then purified, and then combined and formulated with OMVs to give a composition of the invention.

In some embodiments, a polypeptide comprises an amino acid sequence as described above, except that up to 10 amino acids (i.e. 1, 2, 3, 4, 5, 6, 7, 8, 9 or 10) at the N-terminus and/or up to 10 amino acids (i.e. 1, 2, 3, 4, 5, 6, 7, 8, 9 or 10) at the C-terminus are deleted.

Bactericidal Responses

As mentioned above, preferred polypeptides and compositions of the invention can elicit antibody responses that are bactericidal against meningococci. Bactericidal antibody responses are conveniently measured after immunisation of mice and are a standard indicator of vaccine efficacy (e.g. see end-note 14 of ref. 52: also ref. 53). Thus the antibodies will be bactericidal against a test strain in a suitable serum bactericidal assay (SBA).

A fusion fHbp polypeptide can preferably elicit an antibody response which is bactericidal against a meningococcal strain which expresses a v1 fHbp, a meningococcal strain which expresses a v2 fHbp, and also a meningococcal strain which expresses a v3 fHbp. A suitable v1 strain for a SBA test is MC58, which is widely available (e.g. ATCC BAA-335) and was the strain sequenced in reference 23. A suitable v2 strain for a SBA test is M2091 (ATCC 13091). A suitable v3 strain for a SBA test is M01-240355, which is a *Neisseria* MLST reference strains (id 19265 in ref. 54) that has been fully sequenced (see EMBL ID CP002422 [55])

Thus preferred fHbp fusion polypeptides can elicit antibodies in a mouse which are bactericidal against each of strains MC58, M2091, and M01-240355 in a serum bactericidal assay. For example, a composition of the invention can provide a serum bactericidal titer of ≥1:4 using the Goldschneider assay with human complement [56-58], and/or providing a serum bactericidal titer of ≥1:128 using baby rabbit complement.

Immunisation

Polypeptides as discussed above may be used as the active ingredient(s) of immunogenic compositions, and so the invention provides an immunogenic composition (e.g. a vaccine) of the invention comprising polypeptides as discussed above.

The invention also provides a method for raising an antibody response in a mammal, such as a mouse or a human, comprising administering an immunogenic composition of the invention to the mammal. The antibody response is preferably a protective and/or bactericidal antibody response. The invention also provides compositions of the invention for use in such methods.

The invention also provides a method for protecting a mammal, such as a mouse or a human, against a Neisserial (e.g. meningococcal) infection, comprising administering to the mammal an immunogenic composition of the invention.

The invention provides compositions of the invention for use as medicaments (e.g. as immunogenic compositions or as vaccines). In one embodiment, it also provides the use of a fusion polypeptide comprising all three of v1, v2 and v3 meningococcal fHbp, and one or more of (i) a NHBA polypeptide (ii) a NadA polypeptide and/or (iii) meningococcal outer membrane vesicles, in the manufacture of a medicament for preventing Neisserial (e.g. meningococcal) infection in a mammal. In another embodiment, the invention provides the use of meningococcal outer membrane vesicles and one or more of (i) a NHBA polypeptide (ii) a NadA polypeptide and/or (iii) a fusion polypeptide comprising all three of v1, v2 and v3 meningococcal fHbp, in the manufacture of a medicament for preventing Neisserial (e.g. meningococcal) infection in a mammal, wherein the concentration of outer membrane vesicles in the medicament is between 5-30 μg/ml.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia. For instance, they are suitable for active immunisation of individuals against invasive meningococcal disease caused by *N. meningitidis* (for example in serogroup B).

Efficacy of therapeutic treatment can be tested by monitoring Neisserial infection after administration of the composition of the invention. Efficacy of prophylactic treatment can be tested by monitoring immune responses against fHbp, NHBA, NadA and PorA (as appropriate) after administration of the composition. Immunogenicity of compositions of the invention can be determined by administering them to test subjects (e.g. children 12-16 months age, or animal models) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be scroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

The invention may be used to elicit systemic and/or mucosal immunity.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml (e.g. as seen in the BEXSERO™ product).

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. For instance, the BEXSERO™ product is administered as two or three doses given note less than 1 month or not less than 2 months apart, depending on the subject (e.g. infants or others).

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 59. For example, the BEXSERO™ product includes sodium chloride, histidine, sucrose, aluminium hydroxide, and water for injections.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. Compositions suitable for parenteral injection (e.g. to the muscle) are most preferred.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [60]. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed in chapter 7 of ref. 61.

The use of an aluminium hydroxide and/or aluminium phosphate adjuvant is particularly preferred, and polypeptides are generally adsorbed to these salts. These salts include oxyhydroxides and hydroxyphosphates (e.g. see chapters 8 & 9 of ref. 61). The salts can take any suitable form (e.g. gel, crystalline, amorphous, etc.). $Al^{+++}$ should be present at <1 mg/dose.

The most preferred adjuvant is aluminium hydroxide, as used in the BEXSERO™ product. Polypeptides and OMVs in a composition of the invention can be adsorbed to this adjuvant, as seen in the BEXSERO™ product. Aluminium hydroxide can be included at about 1 mg/ml $Al^{+++}$ (i.e. 0.5 mg per 0.5 ml dose)

Further Antigenic Components

A composition of the invention can include further meningococcal polypeptide immunogens in addition to fHbp, NHBA, NadA and/or OMVs. For instance, it might include one or more of NspA, App, NhhA, HmbR, etc.

A composition of the invention can also include a '936' antigen. The 936 antigen was included in the published genome sequence for meningococcal serogroup B strain MC58 [23] as gene NMB2091 (SEQ ID NO: 20 herein). Preferred 936 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 21; and/or (b) comprising a fragment of at least 'n' consecutive amino acids of SEQ ID NO: 21, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 21. The most useful 936 antigens of the invention can elicit antibodies which, after administration to a host mammal, can bind to a meningococcal polypeptide consisting of amino acid sequence SEQ ID NO: 20. The 936 antigen is a good fusion partner for fHbp (e.g. see references 62 & 63).

In addition to meningococcal polypeptide antigens, the composition may include antigens for immunising against other diseases or infections. For example, the composition may include one or more of the following further antigens:

- a saccharide antigen from *N. meningitidis* serogroup A, C. W135 and/or Y, such as the saccharide disclosed in ref. 64 from serogroup C (see also ref. 65) or in ref. 66.
- a saccharide antigen from *Streptococcus pneumoniae* [e.g. 67, 68, 69].
- an antigen from hepatitis A virus, such as inactivated virus [e.g. 70, 71].
- an antigen from hepatitis B virus, such as the surface and/or core antigens [e.g. 71, 72].
- a diphtheria antigen, such as a diphtheria toxoid [e.g. chapter 3 of ref. 73] e.g. the $CRM_{197}$ mutant [e.g. 74].
- a tetanus antigen, such as a tetanus toxoid (e.g. chapter 4 of ref. 73).
- an antigen from *Bordetella pertussis*, such as pertussis holotoxin (PT) and filamentous haemagglutinin (FHA) from *B. pertussis*, optionally also in combination with pertactin and/or agglutinogens 2 and 3 (e.g. refs. 75 & 76).
- a saccharide antigen from *Haemophilus influenzae* B [e.g. 65].
- polio antigen(s) [e.g. 77, 78] such as IPV.
- measles, mumps and/or rubella antigens (e.g. chapters 9, 10 & 11 of ref. 73).
- influenza antigen(s) (e.g. chapter 19 of ref. 73), such as the haemagglutinin and/or neuraminidase surface proteins.
- an antigen from *Moraxella catarrhalis* [e.g. 79].
- an protein antigen from *Streptococcus agalactiae* (group B *streptococcus*) [e.g. 80, 81].
- a saccharide antigen from *Streptococcus agalactiae* (group B *streptococcus*).
- an antigen from *Streptococcus pyogenes* (group A *streptococcus*) [e.g. 81, 82, 83].
- an antigen from *Staphylococcus aureus* [e.g. 84].

The composition may comprise one or more of these further antigens.

Toxic protein antigens may be detoxified where necessary (e.g. detoxification of pertussis toxin by chemical and/or genetic means [76]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates are discussed in more detail below.

Antigens in the composition will typically be present at a concentration of at least 1 μg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (which could be RNA, such as a self-replicating RNA, or DNA, such as a plasmid) encoding the antigen may be used.

In some embodiments a composition of the invention comprises conjugated capsular saccharide antigens from 1, 2, 3 or 4 of meningococcus serogroups A, C, W135 and Y. In other embodiments a composition of the invention comprises at least one conjugated pneumococcal capsular saccharide antigen.

Meningococcus Serogroups Y, W135, C and A

Current serogroup C vaccines (MENJUGATE™ [64,85], MENINGITEC™ and NEISVAC-C™) include conjugated saccharides. MENJUGATE™ and MeningitecMENINGITEC™ have oligosaccharide antigens conjugated to a $CRM_{197}$ carrier, whereas NEISVAC-C™ uses the complete polysaccharide (de-O-acetylated) conjugated to a tetanus toxoid carrier. The MENACTRA™ vaccine contains conjugated capsular saccharide antigens from each of serogroups Y, W135, C and A.

Compositions of the present invention may include capsular saccharide antigens from one or more of meningococcus serogroups Y, W135, C and A, wherein the antigens are conjugated to carrier protein(s) and/or are oligosaccharides. For example, the composition may include a capsular saccharide antigen from: serogroup C; serogroups A and C: serogroups A, C and W135; serogroups A, C and Y; serogroups C, W135 and Y; or from all four of serogroups A, C, W135 and Y.

A typical quantity of each meningococcal saccharide antigen per dose is between 1 μg and 20 μg e.g. about 1 μg, about 2.5 μg, about 4 μg, about 5 μg, or about 10 μg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher).

Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides may be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20: between 12 and 22 for serogroup C; etc.). DP can conveniently be measured by ion exchange chromatography or by colorimetric assays [86].

If hydrolysis is performed, the hydrolysate will generally be sized in order to remove short-length oligosaccharides [65]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 85, as used in MENJUGATE™.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique.

Typical carrier proteins are bacterial toxins, such as diphtheria or tetanus toxins, or toxoids or mutants thereof. The $CRM_{197}$ diphtheria toxin mutant [87] is useful, and is the carrier in the PREVNAR™ product. Other suitable carrier proteins include the *N. meningitidis* outer membrane protein complex [88], synthetic peptides [89,90], heat shock proteins [91,92], pertussis proteins [93,94], cytokines [95], lymphokines [95], hormones [95], growth factors [95], artificial proteins comprising multiple human $CD4^+$ T cell epitopes from various pathogen-derived antigens [96] such as N19 [97], protein D from *H. influenzae* [98-100], pneumolysin [101] or its non-toxic derivatives [102], pneumococcal surface protein PspA [103], iron-uptake proteins [104], toxin A or B from *C. difficile* [105], recombinant *P. aeruginosa* exoprotein A (rEPA) [106], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [107,108, etc.]). Other suitable techniques use carbodiimides, hydrazides, active esters, norborane, p-nitrobenzoic acid, N-hydroxysuccinimide, S—NHS, EDC, TSTU, etc.

Linkages via a linker group may be made using any known procedure, for example, the procedures described in references 109 and 110. One type of linkage involves reductive amination of the polysaccharide, coupling the resulting amino group with one end of an adipic acid linker group, and then coupling a protein to the other end of the adipic acid linker group [111,112]. Other linkers include B-propionamido [113], nitrophenyl-ethylamine [114], haloacyl halides [115], glycosidic linkages [116], 6-aminocaproic acid [117], ADH [118], $C_4$ to $C_{12}$ moieties [119] etc. As an alternative to using a linker, direct linkage can be used. Direct linkages to the protein may comprise oxidation of the polysaccharide followed by reductive amination with the protein, as described in, for example, references 120 and 121.

A process involving the introduction of amino groups into the saccharide (e.g. by replacing terminal =O groups with $-NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

General

The term "comprising" encompasses "including" as well as "consisting" e.g. a composition "comprising" X may consist exclusively of X or may include something additional e.g. X+Y. References to "comprising" (or "comprises", etc.) may optionally be replaced by references to "consisting of" (or "consists of", etc.).

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

"Sequence identity" is preferably determined by the Needleman-Wunsch global alignment algorithm [122], using default parameters (e.g. with Gap opening penalty=10.0, and with Gap extension penalty=0.5, using the EBLOSUM62 scoring matrix). This algorithm is conveniently implemented in the needle tool in the EMBOSS package [123]. Where the application refers to sequence identity to a particular SEQ ID, the identity should be calculated over the entire length of that SEQ ID.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci. The four main hypervirulent clusters are ST32, ST44, ST8 and ST11 complexes.

EXAMPLES

Example 1: The BEXSERO™ Vaccine (for Reference)

The BEXSERO™ product is safe and effective and has been authorised for human use in Europe and elsewhere. It has the following immunogenic ingredients per 0.5 ml dose:

| Immunogen | Quantity | Notes |
|---|---|---|
| fHbp | 50 μg | Fusion polypeptide with NMB2091 at N-terminus |
| NHBA | 50 μg | Fusion polypeptide with NMB1030 at C-terminus |
| NadA | 50 μg | — |
| OMV | 25 μg (total protein) | Strain NZ98/254 (B:4:P1.7-2,4, L1,3) |

These immunogens are adsorbed to an aluminium hydroxide adjuvant (0.5 mg $Al^{+++}$ per dose). The composition also includes NaCl, a histidine buffer, and sucrose.

Example 2: Stabilised and Stabilised Non-Binding Fusion Polypeptides

The inventors have studied two different types of mutation in v2 and v3: firstly, they have identified residues within SEQ ID NO: 2 and SEQ ID NO: 3 which can be modified to increase the polypeptide's stability. Secondly, they have identified residues which decrease binding to human factor H (fH). Mutant fHbp polypeptides comprising both types of mutation, have enhanced properties. Specifically, fHbp mutants that do not bind factor H but which retain immunogenicity are advantageous because the resultant antibody responses are directed towards epitopes in or near the fH-binding site. Following vaccination using wild-type fHbp vaccine antigens, such epitopes may be obscured by factor H binding. The amino acids of most interest are as follows, numbered according to the full-length sequences (SEQ ID NOs: 1 & 3) and also according to the ΔG sequences (SEQ ID NOs: 8 & 9):

| | | Stability** | | fH binding |
|---|---|---|---|---|
| v2 | SEQ ID NO: 1 | Ser-58 | Leu-149 | Glu-266 |
| | SEQ ID NO: 8 | Ser-32 | Leu-123 | Glu-240 |
| v3 | SEQ ID NO: 3 | Ser-63 | Leu-157 | Glu-274 |
| | SEQ ID NO: 7 | Ser-32 | Leu-126 | Glu-243 |

**Where only one of these residues is mutated, it is preferably the leucine

Figure 2:
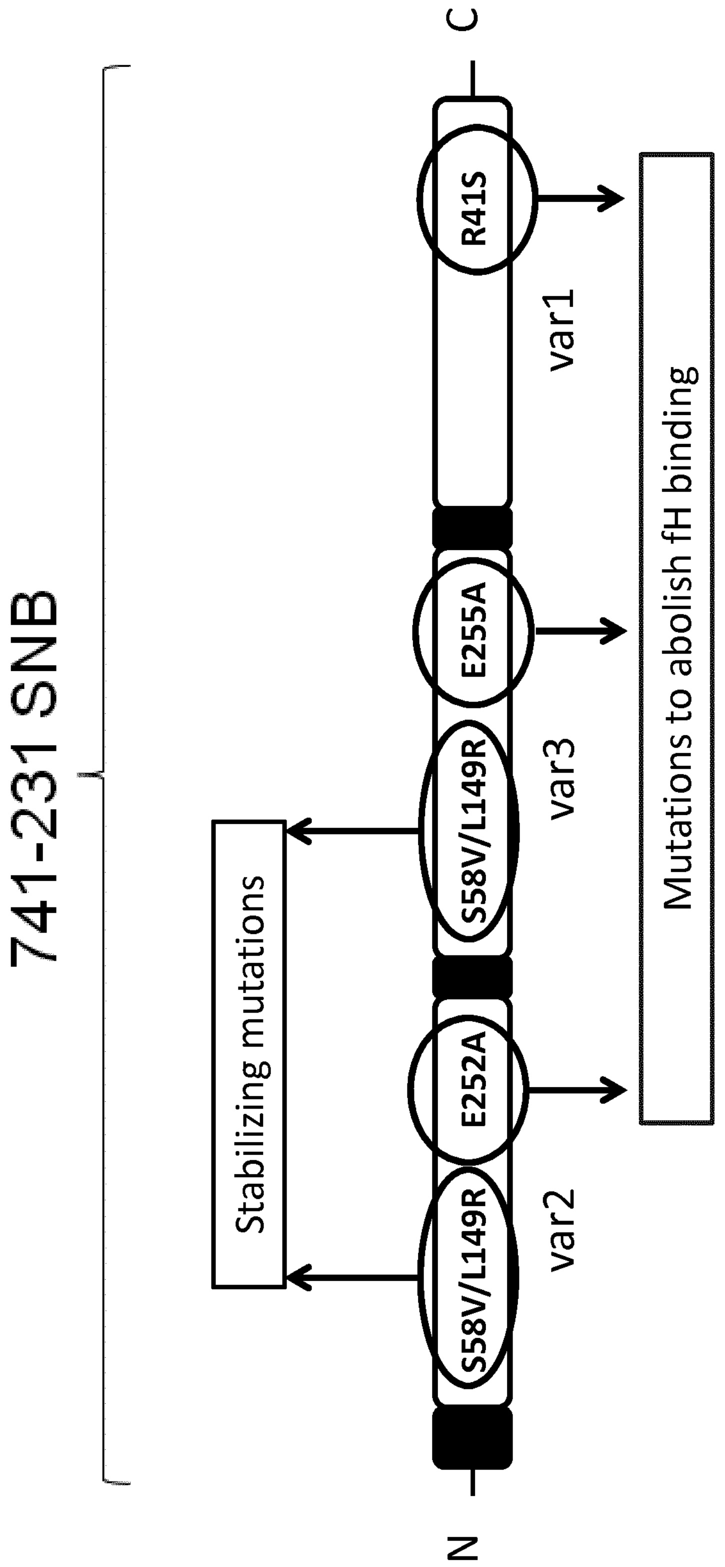
FIG. 2 provides a schematic of stabilising and factor H (fH) non-binding mutations introduced into the v1, v2 and v3 fHbp polypeptides to produce 731 S and 731 SNB fusion proteins.
Figure 3A:
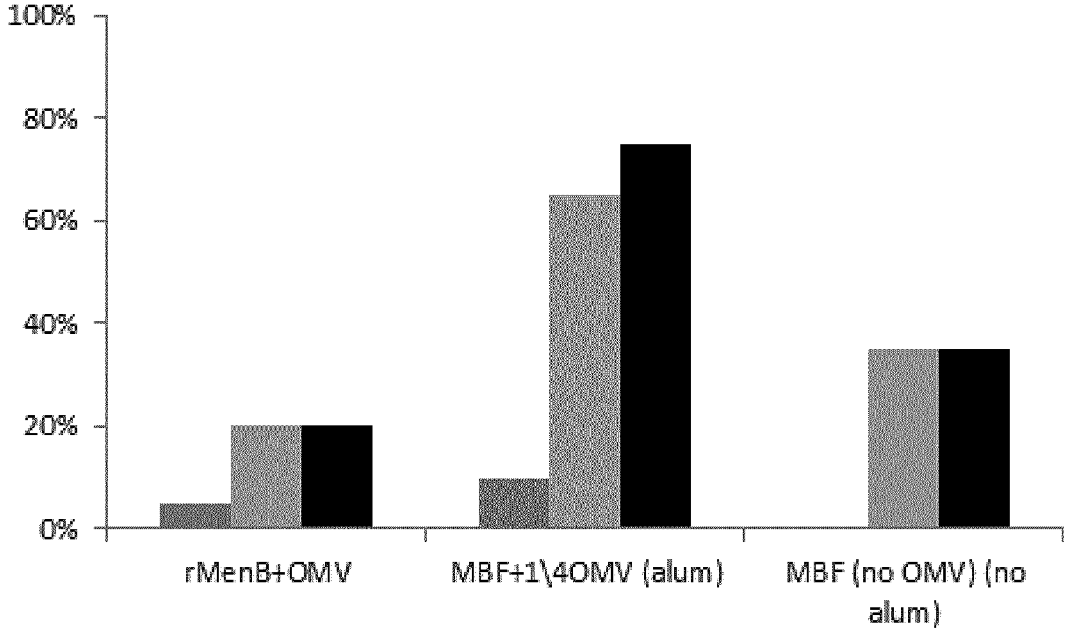
FIG. 3(*a*)-(*g*) demonstrates that compositions comprising the 741-231 fusion (SEQ ID NO:10) and 1/40MV elicits higher GMTs than BEXSERO™ against seven strains tested (3a=v2, 3b=v2, 3c=v3, 3d=v3, 3e=v2, 3f=v2, 3g=v3).
Figure 3B:
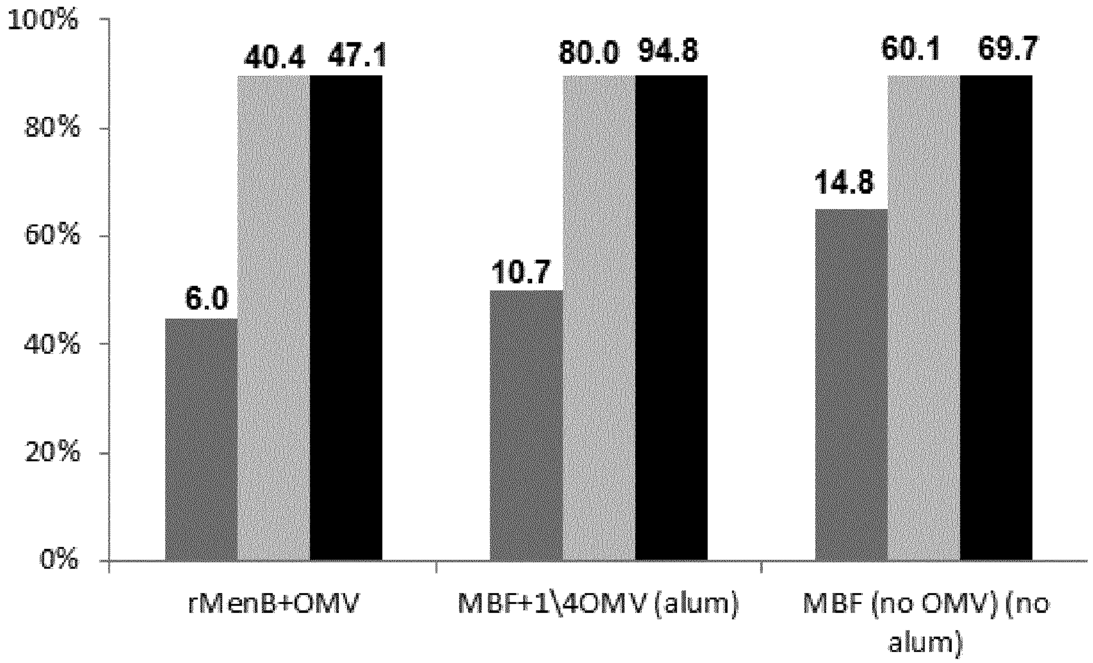
Figure 3C:
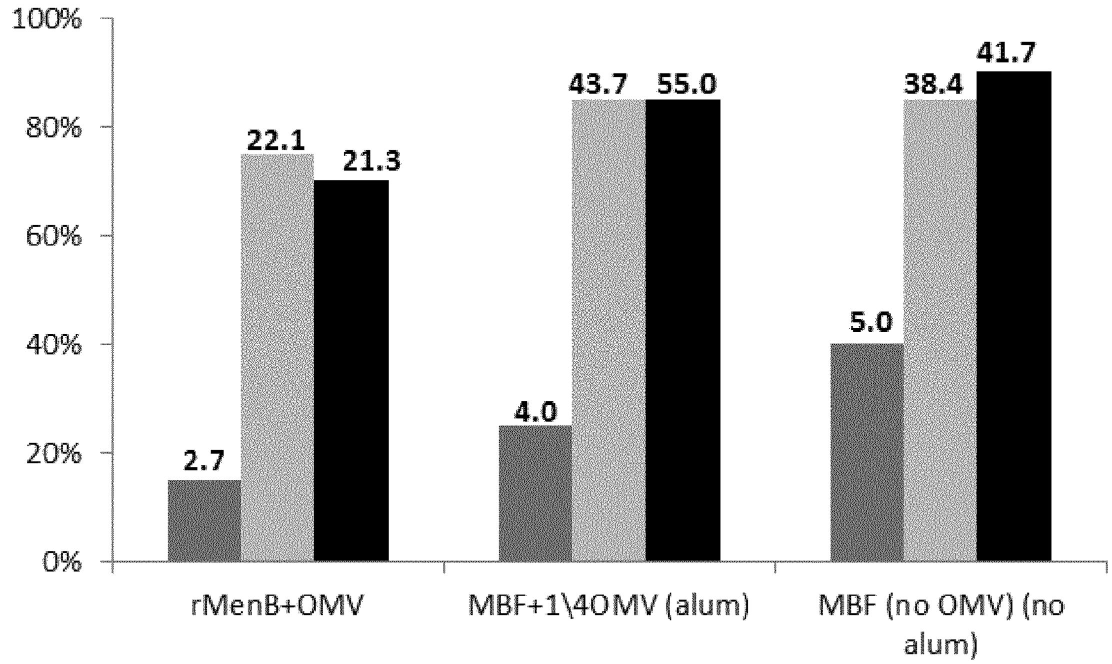
Figure 3D:
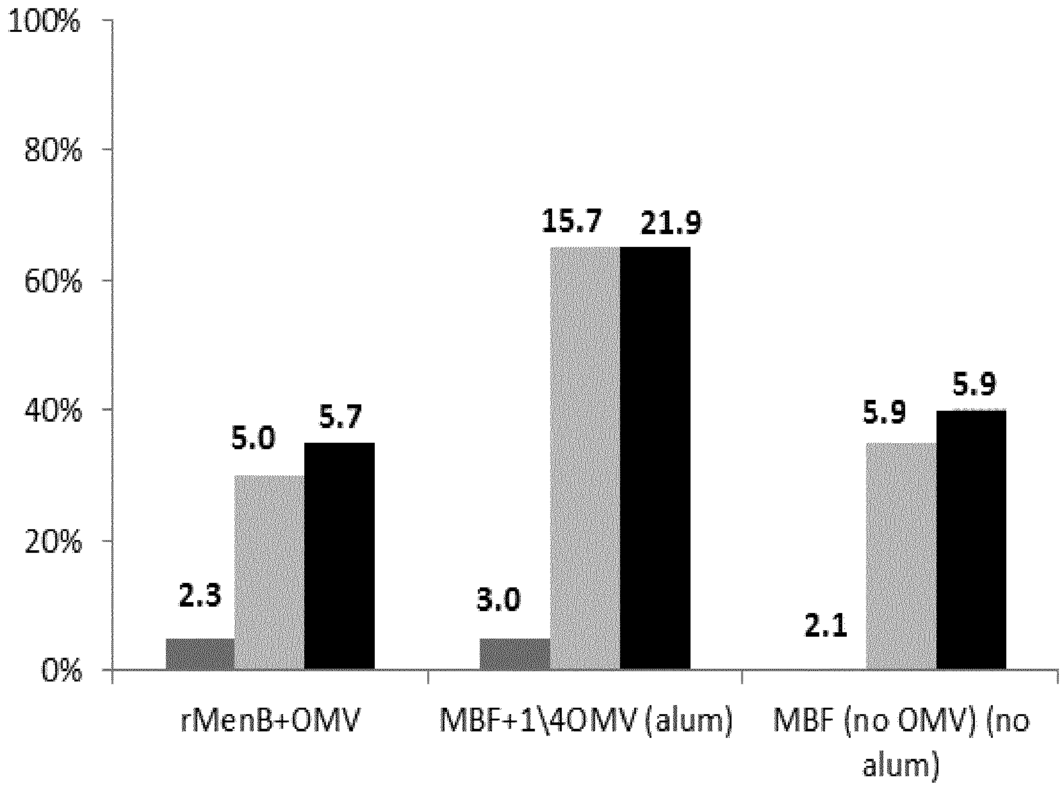
Figure 3E:
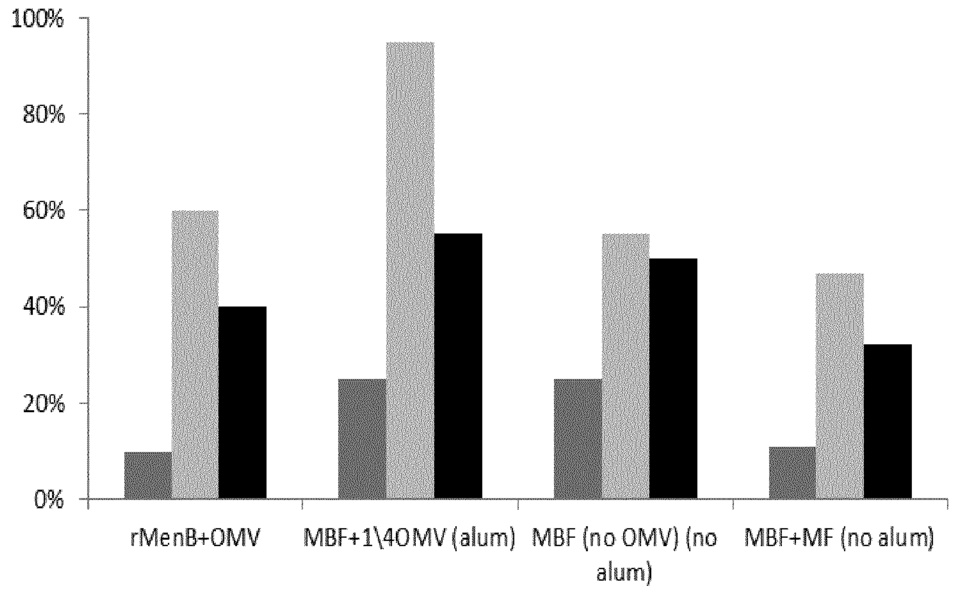
Figure 3F:
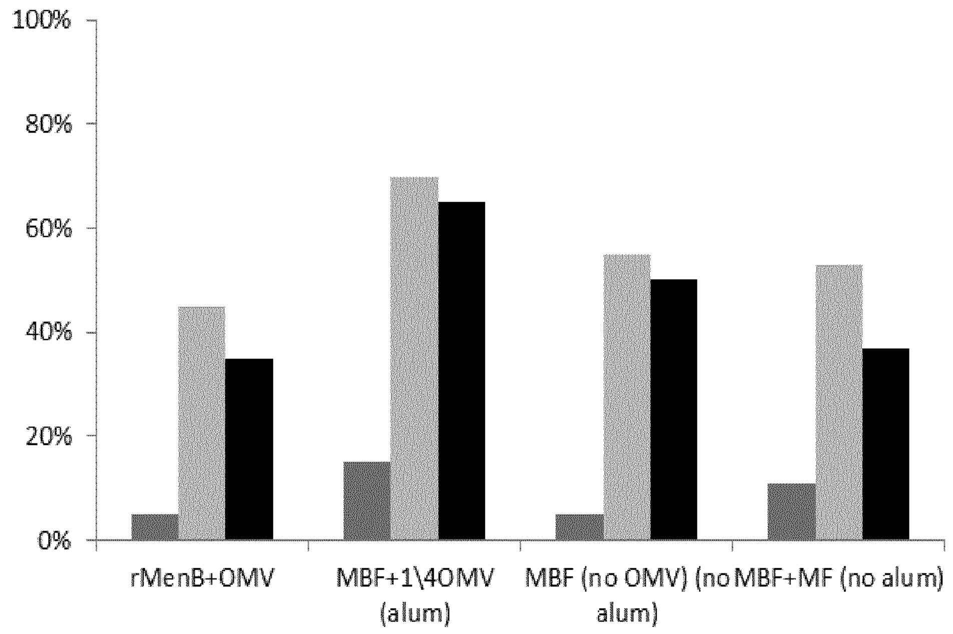
Figure 3G:
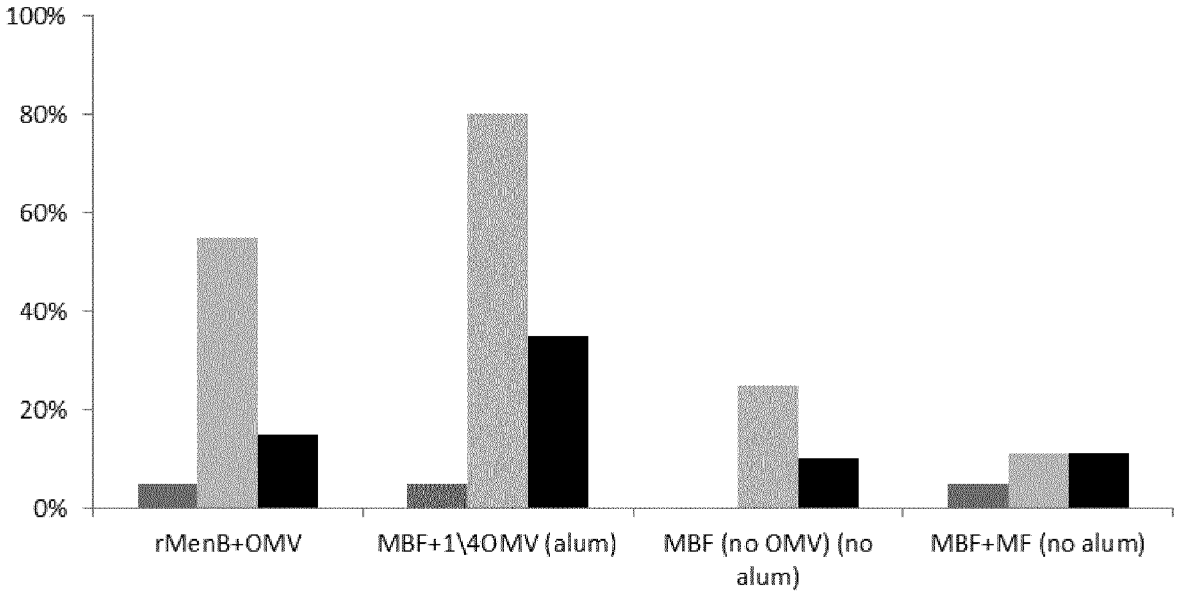

The mutations for stability and fHbp binding were combined into mutant forms of v2 and v3 and fused with a mutant v1 sequence comprising the R41S mutation. Mutants were fused in the order v2-v3-v1 and were joined using linkers, to give 731 SNB (SEQ ID NO: 38). Compared to the three wild-type sequences, this fusion polypeptide includes a total of 7 point mutations (FIG. 2).

Separately, the mutations for stability in v2 and v3 were fused with the 'R41S' mutant v1 sequence in the order v2-v3-v1 and were joined using linkers, to give 731 S (SEQ ID NO: 40). Thus, compared to the three wild-type sequences, this fusion polypeptide includes a total of 5 point mutations (FIG. 2).

The ability of non-fH binding forms of fHbp to elicits SBA titers was tested in transgenic (Tg) mice:

| | rSBA titers obtained against prototypic strains | | |
|---|---|---|---|
| Antigen | Var 1.1 | Var 2.16 | Var 3.42 |
| fHbp fusion SEQ ID NO: 10 | 1024* | 4096 | 8192 |
| fHbp fusion SEQ ID NO: 38 | 16384 | 32768 | >32768 |

These data indicate that non-binding forms of fHbp may be more immunogenic.

Example 3: Substitution of NMB2091-fHbp Fusion

The BEXSERO™ product was modified by replacing the NMB2091-fHbp fusion polypeptide with a "triple fusion" polypeptide of fHbp variants, with v2-v3-v1 from N- to C-terminus. This fusion polypeptide has the amino acid sequence SEQ ID NO: 10. In addition, the OMV component was removed. The two vaccines were compared in mice immunised at days 0, 21 and 35, with sera being assessed at days 34 and 49 against a panel of 15 serogroup B strains in various clonal complexes, MLST, and ET classifications. Antigens were administered at 20 μg/dose, using the adjuvant at 3 mg/ml.

The proportion of strains with SBA titers above various thresholds were as follows:

| Threshold | Original vaccine | Modified vaccine |
|---|---|---|
| ≥128 | 100% | 100% |
| ≥1024 | 93% | 80% |
| >4096 | 53% | 60% |

Use of the v2-v3-v1 fusion polypeptide can thus provide cover against a higher proportion of the panel (60% vs. 53%) at a high anti-MenB SBA Liter (>4096).

Example 4: 4-Fold Reduction of OMV Dosage

The BEXSERO™ product was modified by replacing the NMB2091-fHbp fusion polypeptide with the "triple fusion" fHbp v2-v3-v1 polypeptide (SEQ ID NO: 10) but also by either (i) reducing the OMV dosage 4-fold to 12.5 μg/ml or (ii) removing the OMV component. Thus three compositions were prepared:

| Group | Protein immunogens | | | OMVs |
|---|---|---|---|---|
| M | NMB2091-fHbp | NHBA-NMB1030 | NadA | 50 μg/ml |
| C | fHbp-v2-v3-v1 | NHBA-NMB1030 | NadA | 12.5 μg/ml |
| S | fHbp-v2-v3-v1 | NHBA-NMB1030 | NadA | — |

To assess immunogenicity of these three vaccines human subjects received three doses at monthly intervals (months 0, 1, 2). Sera were taken at months 0, 1, 2 and 3, and then 6 months after the third dose (month 8), for assessment against a panel of relevant strains. Titers (GMT) were as follows:

| | M | C | S |
|---|---|---|---|
| Strain H44/76 | | | |
| Time zero | 1.36 | 2.16 | 1.55 |
| 1 month | 30 | 52 | 15 |
| 2 months | 97 | 91 | 48 |
| 3 months | 102 | 99 | 59 |
| 8 months | 25 | 33 | 12 |
| Strain 5/99 | | | |
| Time zero | 2.47 | 3.01 | 2.17 |
| 1 month | 70 | 75 | 56 |
| 2 months | 173 | 140 | 157 |
| 3 months | 237 | 236 | 365 |
| 8 months | 77 | 83 | 106 |
| Strain NZ98/254 | | | |
| Time zero | 1.21 | 2.04 | 1.73 |
| 1 month | 9.45 | 29 | 3.19 |
| 2 months | 13 | 12 | 4.4 |
| 3 months | 16 | 24 | 6.49 |
| 8 months | 3.55 | 8.02 | 3.55 |
| Strain M14459 | | | |
| Time zero | 1.86 | 2.48 | 2.16 |
| 2 months | 30 | 24 | 16 |
| 3 months | 34 | 31 | 19 |
| Strain UK364 | | | |
| Time zero | 1.35 | 1.97 | 2.07 |
| 2 months | 37 | 72 | 70 |
| 3 months | 56 | 113 | 112 |

Pooled patient sera were used to assess coverage of a panel of 7 MenB strains which express a v1 fHbp. A similar number of strains was adequately covered in each group, but titers (GMT) were highest in group C:

| | M | C | S |
|---|---|---|---|
| Time zero | <10 | <10 | <10 |
| 3 months | 70 | 140 | 40 |
| 8 months | 15 | 50 | 10 |

Single patient sera were tested against a panel of 6 MenB strains which express a v2 or v3 fHbp (one strain was tested twice). Again, titers (GMT) were highest in group C:

| | M | C | S |
|---|---|---|---|
| Strain M14549 (v2) | | | |
| Time zero | 1.4 | 1.5 | 1.1 |
| 2 months | 3.8 | 15.0 | 6.2 |
| 3 months | 3.6 | 21.4 | 6.6 |
| Strain M12566 (v2) | | | |
| Time zero | 6.0 | 10.7 | 14.8 |
| 2 months | 40.4 | 80.0 | 60.1 |
| 3 months | 47.1 | 94.8 | 69.7 |
| Strain UK355 (v3) | | | |
| Time zero | 2.7 | 4.0 | 5.0 |
| 2 months | 22.1 | 43.7 | 38/4 |
| 3 months | 21.3 | 55.0 | 41.7 |
| Strain M1239 (v3) | | | |
| Time zero | 2.3 | 3.0 | 2.1 |
| 2 months | 5.0 | 15.7 | 5.9 |
| 3 months | 5.7 | 21.9 | 5.9 |

-continued

| | M | C | S |
|---|---|---|---|
| Strain M1239 (v3) | | | |
| Time zero | 1.2 | 1.6 | 1.1 |
| 2 months | 5.9 | 18.4 | 2.8 |
| 8 months | 1.9 | 4.1 | 1.6 |
| Strain UK293 (v2) | | | |
| Time zero | 1.6 | 2.7 | 2.2 |
| 2 months | 9.2 | 52.0 | 7.0 |
| 8 months | 4.3 | 11.7 | 5.9 |
| Strain UK414 (v2) | | | |
| Time zero | 1.4 | 2.1 | 1.6 |
| 2 months | 5.1 | 22.6 | 8.3 |
| 8 months | 3.1 | 10.9 | 6.3 |

Furthermore, the proportion of immunised subjects with a SBA titer above 1:8 was generally higher in group C compared to groups M and S e.g. 80% or more for strain M1239 after 3 doses compared to 50% or less in the other two groups.

RCD curves (reverse cumulative distribution) of SBA titers also showed a better profile e.g. FIG. 1 shows a curve for 3 month sera against strain UK293, with group C being clearly above the others.

Pooled patient sera were used to assess coverage of a panel of 26 MenB strains which express a v2 or v3 fHbp. Again, titers (GMT) were highest in group C:

| | M | C | S |
|---|---|---|---|
| 3 months | 23 | 91 | 25 |
| 8 months | 7 | 43 | 9 |

These data thus show that vaccine ‘C’, in which the fHbp immunogen has been replaced and the OMV dosage was reduced 4-fold, is not inferior to the BEXSERO™ vaccine. Indeed, single-subject and pooled sera both show better seroresponse rates, higher GMTs, and increased strain coverage for vaccine ‘C’ when compared to the BEXSERO™ vaccine.

Example 5: Antibody Avidity

Avidity of antibodies from patients in groups ‘C’ and ‘S’ was compared using a Gyrolab-based system which includes a wash step using a chaotropic agent to detach low affinity antibodies from antigen, giving in ‘Avidity Index’ as the percentage of high affinity anti-v1.fHbp antibodies out of total v1.fHbp-specific antibodies. Twenty separate sera were assessed 1 month after the first dose and 1 month after the third dose. In addition, SBA titres were assessed against strain H44/76, and correlations between avidity index and SBA titre (log 2) were determined.

Results (R and p by Pearson correlation) were as follows:

| | 1 month post-1 | | 1 month post-3 | |
|---|---|---|---|---|
| | R | p | R | p |
| C | 0.693 | 0.001 | 0.4667 | 0.0381 |
| S | 0.3565 | 0.1229 | 0.101 | 0.6718 |

Thus there was a significant correlation between SBA titre and avidity index in group ‘C’ at both time points, but not in group 'S'. In subjects who received the vaccine with 12.5 μg/ml OMV the Avidity Index correlates with the SBA titres, which suggests that the presence of OMV has a positive impact on the quality of the induced antibodies. Overall, in subjects who received OMV the trend is that the bactericidal titers are higher and they correlate with the avidity of the antibodies induced by the vaccine formulation.

A subpanel of var2/3 strains was selected for single subject sera testing on the basis of following criteria: (i) Strains not covered by BEXSERO™ in previous clinical trials, (ii) Strains belong to relevant clonal complexes, (iii) Strains express epidemiologically relevant fHbp subvariants, (iv) Level of fHbp expression is medium, (v) Strains are specifically killed by 741-231 (competitive hSBA). Results are shown in FIGS. 3(*a*) to 3(*g*) demonstrating that 741-231+¼OMV+alum elicits higher GMT against the 7 strains tested. Thus, hSBA testing indicates that formulations including 741-231 fusion are not inferior to BEXSERO™. In fact, both single subject sera and pooled sera analysis on var2/3 strains show better seroresponse rates, higher GMT titers and increased strain coverage for formulation including 741-231+¼OMV+alum.

Example 6: Reduction of OMV Dosage and Use of 731 'S' and 731 'SNB'

The BEXSERO™ product was modified by replacing the NMB2091-fHbp fusion polypeptide with the "triple fusion" stabilised or stabilised non-binding fHbp v2-v3-v1 polypeptides (SEQ ID NOs:40 and 38 respectively) but also by reducing the OMV dosage to 10 μg/ml or 2.5 μg/ml:

| Group | Protein immunogens | | | OMVs |
|---|---|---|---|---|
| 1 | NMB2091-fHbp | NHBA-NMB1030 | NadA | 10 μg/ml |
| 2 | fHbp-v2-v3-v1 SNB | NHBA-NMB1030 | NadA | 2.5 μg/ml |
| 3 | fHbp-v2-v3-v1 S | NHBA-NMB1030 | NadA | 2.5 μg/ml |

To prepare mice antisera, 20 μg of NadA. NHBA-NMB1030 and either NMB2091-fHbp, fHbp 231S or fHbp 231SNB with 10 μg or 2.5 μg of OMV derived from strain NZ98/254 were used to immunize 6-week-old CD1 female mice (Charles River). Eight mice per group were used. The antigens were administered intraperitoneally together with aluminium hydroxide (3 mg/ml) on days 0, 21 and 35. Sera were collected 2 weeks after the final bleed and heat-inactivated for 30 min at 56° C. before testing.

Serum Bactericidal Assay with Animal Sera and Human Complement

Serum bactericidal activity against Nm strains was evaluated as previously described. Human serum or plasma from a healthy adult (with no intrinsic bactericidal activity when tested at a final concentration of 25 or 50%) was used as a complement source. Serum bactericidal titers were defined as the serum dilution resulting in 50% decrease in colony forming units (CFU) per ml after 60 min incubation of bacteria with reaction mixture, compared to control CFU per ml at time 0.

The lowest dilution tested for each sera was 1:16 (limit of detection). Titers below the limit of detection were set to half that limit for the purposes of analysis and positive threshold was defined as a 4 fold rise compared to this value (i.e 32). Pooled serum derived from mice immunized with BEXSERO™ formulation were under the positive threshold for 14 strains among the 34 strain tested, while pooled sera derived from 2$^{nd}$ generation formulation were under the limit of detection for only 1 strain in case of vaccine formulation containing fHbp 231SNB and for 1 strains in case of formulation containing fHbp 231S.

hSBA data reported in the below table showed an increase of coverage elicited by the vaccine formulations containing fHbp 231S or fHbp 231SNB compare to BEXSERO™ in the panel of 34 strains tested:

| MenB strains | | | hSBA results with different formulations | | |
|---|---|---|---|---|---|
| | ID | fHbp subvariant | Bexsero | 741-231 SNB + 961c + 287-953 + ¼ OMV | 741-231 S + 961c + 287-953 + ¼ OMV |
| Bexsero reference strains | NVD000007 | 2.23 | >8192 | >8192 | >8192 |
| | NVD000005 | 2.16 | 2048 | 4096 | 2048 |
| | NVD000023 | 3.31 | 4096 | 4096 | 8192 |
| | NVD002240 | 2.553 | 32 | 512 | 128 |
| | NVD000025 | 1.1 | >8192 | >8192 | >8192 |
| | NVD001491 | 1.180 | 1024 | 1024 | 512 |
| | NVD000049 | 1.14 | 4096 | 4096 | 2048 |
| MenB strains carrying var1 fHbp | NVD001706 | 1.1 | 4096 | 4096 | 4096 |
| | NVD001889 | 1.4 | 1024 | 2048 | 2048 |
| | NVD001402 | 1.4 | 512 | 1024 | 1024 |
| | NVD001908 | 1.13 | 512 | 1024 | 1024 |
| | NVD001244 | 1.14 | 2048 | 2048 | 2048 |
| | NVD003213 | 1.15 | 2048 | 1024 | 2048 |
| | NVD001080 | 1.15 | 512 | 512 | 512 |
| | NVD000185 | 1.15 | 512 | 512 | 512 |
| | NVD000758 | 1.256 | <16 | 64 | <16 |
| MenB strains carrying var2 fHbp | NVD002368 | 2.16 | 64 | 1024 | 512 |
| | NVD002500 | 2.16 | <16 | 512 | 512 |
| | NVD000926 | 2.16 | 8192 | >8192 | 4096 |
| | NVD002552 | 2.19 | 16 | 512 | 1024 |
| | NVD001277 | 2.19 | <16 | 1024 | 2048 |
| | NVD001057 | 2.19 | 32 | 1024 | 512 |
| | NVD001342 | 2.19 | 64 | 2048 | 1024 |
| | NVD001391 | 2.19 | <16 | 512 | 512 |

-continued

| MenB strains | | | hSBA results with different formulations | | |
|---|---|---|---|---|---|
| | ID | fHbp subvariant | Bexsero | 741-231 SNB + 961c + 287-953 + ¼ OMV | 741-231 S + 961c + 287-953 + ¼ OMV |
| MenB strains carrying var3 fHbp | NVD001288 | 2.21 | <16 | 512 | 512 |
| | NVD002690 | 2.24 | <16 | 256 | 256 |
| | NVD001287 | 2.24 | 16 | 128 | 256 |
| | NVD000038 | 3.28 | <16 | 64 | 64 |
| | NVD000084 | 3.30 | <16 | 1024 | 2048 |
| | NVD003212 | 3.31 | <16 | 512 | 256 |
| | NVD003364 | 3.42 | <16 | 2048 | 2048 |
| | NVD002424 | 3.42 | <16 | 1024 | 1024 |
| | NVD003727 | 3.42 | <16 | <16 | <16 |

It will be understood that the invention is described above by way of example only and modifications may be made whilst remaining within the scope and spirit of the invention.

REFERENCES

[1] Carter (2013) *BioDrugs* 27:263-74.
[2] WO99/57280.
[3] Masignani et al. (2003) *J Exp Med* 197:789-799.
[4] Welsch et al. (2004) *J Immunol* 172:5605-15.
[5] Hou et al. (2005) *J Infect Dis* 192(4):580-90.
[6] WO03/063766.
[7] Fletcher et al. (2004) *Infect Immun* 72:2088-2100.
[8] Zhu et al. (2005)*Infect Immun* 73(10):6838-45.
[9] Cendron et al. (2011) *Acta Crystallogr Sect F Struct Biol Cryst Commun.* 67:531-5.
[10] Mascioni et al. (2009) *J Biol Chem* 284:8738-46.
[11] Pizza et al. (2008) *Vaccine* 26 Suppl 8:I46-8.
[12] Malito et al. (2013) *PNAS USA* 110:3304-9.
[13] Marshall et al. (2012) *Pediatr Infect Dis J* 31:1061-8.
[14] McNeil et al. (2013) *Microbiol Mol Biol Rev* 77:234-52.
[15] Serruto et al. (2012) *Vaccine* 30 Suppl 2: B87-97.
[16] Scarselli et al. (2011) *Sci Transl Med* 3:91ra62.
[17] Beernink et al. (2008)*Infect Immun* 76:423240.
[18] Scarselli et al. (2009) *J Mol Biol* 386:97-108.
[19] Giuntini et al. (2012) *PLoS One* 7:e34272.
[20] Vu et al. (2012) *Sci Rep* 2:341.
[21] Faleri et al (2013) *FASEB J* fj.13-239012.
[22] Beernink et al. (2011) *J Immunol* 186:3606-14.
[23] Tettelin et al (2000) *Science* 287:1809-1815.
[24] WO00/66741.
[25] WO02/09643.
[26] Katial et al. (2002) *Infect Immun* 70:702-707.
[27] WO01/52885.
[28] European patent 0301992.
[29] Frasch et al. (2001) chapter 7 of *Methods in Molecular Medicine*, volume 66 ('*Meningococcal Vaccines: Methods and Protocols*', eds. Pollard & Maiden).
[30] Bjune et al. (1991) *Lancet* 338(8775):1093-1096.
[31] Fukasawa et al. (1999) *Vaccine* 17:2951-2958.
[32] WO02/09746.
[33] Rosenqvist et al. (1998) *Dev. Biol. Stand.* 92:323-333.
[34] European patent 0011243.
[35] Fredriksen et al. (1991) *NIPH Ann.* 14(2):67-80.
[36] WO01/91788.
[37] WO2004/019977.
[38] U.S. Pat. No. 6,558,677.
[39] WO01/09350.
[40] European patent 0449958.
[41] EP-A-09%712.
[42] EP-A-0680512.
[43] WO02/062378.
[44] WO99/59625.
[45] U.S. Pat. No. 6,180,111.
[46] WO01/34642.
[47] Peeters et al. (19%) *Vaccine* 14:1008-1015.
[48] Vermont et al. (2003) *Infect Immun* 71:1650-1655.
[49] WO2004/014417.
[50] WO2005/004908.
[51] WO2011/036562.
[52] Pizza et al. (2000) *Science* 287:1816-1820.
[53] WO2007/028408.
[54] (hypertext transfer protocol)://pubmist.org/*neisseria,*
[55] Budroni et al. (2011) *PNAS USA* 108:4494-99.
[56] Goldschneider et al. (1969) *J. Exp. Med.* 129:1307-26.
[57] Santos et al. (2001) *Clinical and Diagnostic Laboratory Immunology* 8:616-23.
[58] Frasch et al. (2009) Vaccine 27S:B112-6.
[59] Gennaro (2000) *Remington: The Science and Practice of Pharmacy.* 20th edition. ISBN: 0683306472.
[60] WO03/009869.
[61] Vaccine Design . . . (1995) eds. Powell & Newman. ISBN: 030644867X. Plenum.
[62] Giuliani et al. (2006) *Proc Natl Acad Sci USA.* 103: 10834-9.
[63] WO2004/032958.
[64] Costantino et al. (1992) *Vaccine* 10:691-698.
[65] Costantino et al. (1999) *Vaccine* 17:1251-1263.
[66] WO03/007985.
[67] Watson (2000)*Pediatr Infect Dis J* 19:331-332.
[68] Rubin (2000) *Pediatr Clin North Am* 47:269-285, v.
[69] Jedrzejas (2001) *Microbiol Mol Biol Rev* 65:187-207.
[70] Bell (2000) *Pediatr Infect Dis. J* 19:1187-1188.
[71] Iwarson (1995) *APMIS* 103:321-326.
[72] Gerlich et al. (1990) *Vaccine* 8 Suppl:S63-68 & 79-80.
[73] *Vaccines* (1988) eds. Plotkin & Mortimer. ISBN 0-7216-1946-0.
[74] Del Guidice et al. (1998) *Molecular Aspects of Medicine* 19:1-70.
[75] Gustafsson et al. (1996)*N. Engl. J Med* 334:349-355.
[76] Rappuoli et al (1991) *TIBTECH* 9:232-238.
[77] Sutter et al. (2000) *Pediatr Clin North Am* 47:287-308.
[78] Zimmerman & Spann (1999) *Am Fam Physician* 59:113-118, 125-126.
[79] McMichael (2000) Vaccine 19 Suppl 1:S101-107.
[80] Schuchat (1999) *Lancet* 353(9146):51-6.
[81] WO02/34771.
[82] Dale (1999) *Infect Dis Clin North Am* 13:227-43, viii.

[83] Ferretti et al. (2001) *PNAS USA* 98: 4658-4663.
[84] Kuroda et al. (2001) *Lancet* 357(9264):1225-1240: see also pages 1218-1219.
[85] Jones (2001) *Curr Opin Investig Drugs* 2:47-49.
[86] Ravenscroft et al. (1999) *Vaccine* 17:2802-2816.
[87] Research Disclosure, 453077 (January 2002).
[88] EP-A-0372501.
[89] EP-A-0378881.
[90] EP-A-0427347.
[91] WO93/17712.
[92] WO94/03208.
[93] WO98/58668.
[94] EP-A-0471177.
[95] WO91/01146.
[96] Falugi et al. (2001) *Eur J Immunol* 31:3816-3824.
[97] Baraldo et al. (2004) *Infect Immun* 72(8):4884-7.
[98] EP-A-0594610.
[99] Ruan et al. (1990) *J Immunol* 145:3379-3384.
[100] WO00/56360.
[101] Kuo et al. (1995) *Infect Immun* 63:2706-13.
[102] Michon et al. (1998) *Vaccine.* 16:1732-41.
[103] WO02/091998.
[104] WO01/72337.
[105] WO00/61761.
[106] WO00/33882
[107] Lees et al. (1996) *Vaccine* 14:190-198.
[108] WO95/08348.
[109] U.S. Pat. No. 4,882,317
[110] U.S. Pat. No. 4,695,624
[111] Porro et al. (1985)*Mol Immunol* 22:907-919.s
[112] EP-A-0208375
[113] WO00/10599
[114] Gever et al. *Med. Microbiol. Immunol,* 165: 171-288 (1979).
[115] U.S. Pat. No. 4,057,685.
[116] U.S. Pat. Nos. 4,673,574; 4,761,283; 4,808,700.
[117] U.S. Pat. No. 4,459,286.
[118] U.S. Pat. No. 4,965,338
[119] U.S. Pat. No. 4,663,160.
[120] U.S. Pat. No. 4,761,283
[121] U.S. Pat. No. 4,356,170
[122] Needleman & Wunsch (1970) *J. Mol. Biol.* 48, 443453.
[123] Rice et al. (2000) *Trends Genet* 16:276-277.

SEQUENCE LISTING

```
>SEQ ID NO: 1 [MC58, v1]
MNRTAFCCLSLITALILTACSSGGGGVAADIGAGLADALTAPLDHKDKGLQSLILDQSVRKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ

>SEQ ID NO: 2 [2996, v2]
MNRTAFCCLSLTAALILTACSSGGGGVAADIGAGLADALTAPLDHKDKSLQSLILDQSVRKNEKLKLAA
QGAEKTYGNGDSLNIGKLKNDKVSREDFIRQIEVDGQLITLESGEFQIYKQDHSAVVALQIEKINNPDK
IDSLINQRSELVSGLGGEHTAFNQLPDGKAEYHGKAFSSDDAGGKLTYTIDFAAKQGHGKIEHLKTPEQ
NVELAAAELKADEKSHAVILGDTRYGSEEKGTYHLALFGDRAQEIAGSATVKIGEKVHEIGIAGKQ

>SEQ ID NO: 3 [M1239, v3]
MNRTAFCCLSLITALILTACSSGGGGSGGGGVAADIGTGLADALTAPLDHKDKGLKSLTLEDSIPQNGT
LTLSAQGAEKTFKAGDKDNSLNIGKLKNDKISREDFVQKIEVDGQTITLASGEFQIYKQNHSAVVALQI
EKINNPDKTDSLINQRSELVSGLGGEHTAFNQLPGGKAEYHGKAFSSDDPNGRLHYSIDETKKQGYGRI
EHLKTLEQNVELAAAELKADEKSHAVILGDTRYGSEEKGTYHLALFGDRAQEIAGSATVKIGEKVHEIG
IAGKQ

>SEQ ID NO: 4 [MC58, v1, mature]
CSSGGGGVAADIGAGLADALTAPLDHKDKGLQSLILDQSVRKNEKLKLAAQGAEKTYGNGDSLNIGKLK
NDKVSREDFIRQIEVDGQLITLESGEFQVYKQSHSALTAFQTEQIQDSEHSGKMVAKRQFRIGDIAGEH
TSFDKLPEGGRATYRGTAFGSDDAGGKLTYTIDFAAKQGNGKIEHLKSPELNVDLAAADIKPDGKRHAV
ISGSVLYNQAEKGSYSLGIEGGKAQEVAGSAEVKTVNGIRHIGLAAKQ

>SEQ ID NO: 5 [2996 mature]
CSSGGGGVAADIGAGLADALTAPLDHKDKSLQSLILDQSVRKNEKLKLAAQGAEKTYGNGDSLNIGKLK
NDKVSREDFIRQIEVDGQLITLESGEFQIYKQDHSAVVALQIEKINNPDKIDSLINQRSELVSGLGGEH
TAFNQLPDGKAEYHGKAFSSDDAGGKLTYTIDFAAKQGHGKIEHLKTPEQNVELAAAELKADEKSHAVI
LGDTRYGSEEKGTYHLALFGDRAQEIAGSATVKIGEKVHEIGIAGKQ

>SEQ ID NO: 6 [M1239, mature]
CSSGGGGSGGGGVAADIGTGLADALTAPLDHKDKGLKSLTLEDSIPQNGTLTLSAQGAEKTFKAGDKDN
SLNIGKLKNDKISREDEVQKIEVDGQIITLASGEFQIYKQNHSAVVALQIEKINNPDKTDSLINQRSFL
VSGLGGEHTAFNQLPGGKAEYHGKAFSSDDPNGRLHYSIDETKKQGYGRIEHLKTLEQNVELAAAELKA
DEKSHAVILGDTRYGSEEKGTYHLALFGDRAQEIAGSATVKIGEKVHEIGIAGKQ

>SEQ ID NO: 7 [MC58, ΔG]
VAADIGAGLADALTAPLDHKDKGLQSLILDQSVRKNEKLKLAAQGAEKTYGNGDSLNIGKLKNDKVSRF
DFIRQIEVDGQLITLESGEFQVYKQSHSALTAFQTEQIQDSEHSGKMVAKRQFRIGDIAGEHTSFDKLP
EGGRATYRGTAFGSDDAGGKLTYTIDFAAKQGNGKIEHLKSPELNVDLAAADIKPDGKRHAVISGSVLY
NQAEKGSYSLGIEGGKAQEVAGSAEVKTVNGIRHIGLAAKQ

>SEQ ID NO: 8 [2996 ΔG]
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSELVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQ
```

-continued

SEQUENCE LISTING

>SEQ ID NO: 9 [M1239, ΔG]
VAADIGTGLADALTAPLDHKDKGLKSLTLEDSIPQNGTLTLSAQGAEKTFKAGDKDNSLNIGKLKNDKI
SREDEVQKIEVDGQIITLASGEFQIYKQNHSAVVALQIEKINNPDKTDSLINQRSFLVSGLGGEHTAFN
QLPGGKAEYHGKAFSSDDPNGRLHYSIDETKKQGYGRIEHLKTLEQNVELAAAELKADEKSHAVILGDT
RYGSEEKGTYHLALFGDRAQEIAGSATVKIGEKVHEIGIAGKQ

>SEQ ID NO: 10 [fHbp fusion polypeptide]
MGPDSDRLQQRRVAADIGAGLADALTAPLDHKDKSLQSLTLDQSVRKNEKLKLAAQGAEKTYGNGDSLN
TGKLKNDKVSRFDFIRQIEVDGQLITLESGEFQIYKQDHSAVVALQIEKINNPDKIDSLINQRSFLVSG
LGGEHTAFNQLPDGKAEYHGKAFSSDDAGGKLTYTIDFAAKQGHGKIEHLKTPEQNVELAAAELKADEK
SHAVILGDTRYGSEEKGTYHLALFGDRAQEIAGSATVKIGEKVHEIGIAGKQGSGPDSDRLQQRRVAAD
IGTGLADALTAPLDHKDKGLKSLTLEDSIPQNGTLTLSAQGAEKTFKAGDKDNSLNTGKLKNDKISRFD
FVQKIEVDGQTITLASGEFQIYKQNHSAVVALQIEKINNPDKTDSLINQRSFLVSGLGGEHTAFNQLPG
GKAEYHGKAFSSDDPNGRLHYSIDFTKKQGYGRIEHLKTLEQNVELAAAELKADEKSHAVILGDTRYGS
EEKGTYHLALFGDRAQEIAGSATVKIGEKVHEIGIAGKQGSGGGGVAADIGAGLADALTAPLDHKDKGL
QSLTLDQSVRKNEKLKLAAQGAEKTYGNGDSLNTGKLKNDKVSRFDFIRQIEVDGQLITLESGEFQVYK
QSHSALTAFQTEQIQDSEHSGKMVAKRQFRIGDIAGEHTSFDKLPEGGRATYRGTAFGSDDAGGKLTYT
IDFAAKQGNGKIEHLKSPELNVDLAAADIKPDGKRHAVISGSVLYNQAEKGSYSLGIFGGKAQEVAGSA
EVKTVNGIRHIGLAAKQ >SEQ ID NO: 11 [NHBA, MC58]
MFKRSVIAMACIFALSACGGGGGGSPDVKSADTLSKPAAPVVSEKETEAKEDAPQAGSQGQGAPSAQGS
QDMAAVSEENTGNGGAVTADNPKNEDEVAQNDMPQNAAGTDSSTPNHTPDPNMLAGNMENQATDAGESS
QPANQPDMANAADGMQGDDPSAGGQNAGNTAAQGANQAGNNQAAGSSDPIPASNPAPANGGSNFGRVDL
ANGVLIDGPSQNITLTHCKGDSCSGNNFLDEEVQLKSEFEKLSDADKISNYKKDGKNDKFVGLVADSVQ
MKGINQYIIFYKPKPTSFARFRRSARSRRSLPAEMPLIPVNQADTLIVDGEAVSLTGHSGNIFAPEGNY
RYLTYGAEKLPGGSYALRVQGEPAKGEMLAGAAVYNGEVLHFHTENGRPYPTRGRFAAKVDFGSKSVDG
IIDSGDDLHMGTQKFKAAIDGNGFKGTWTENGSGDVSGKEYGPAGEEVAGKYSYRPTDAEKGGEGVFAG
KKEQD >SEQ ID NO: 12 [NHBA fragment]
SPDVKSADTLSKPAAPVVSEKETEAKEDAPQAGSQGQGAPSAQGSQDMAAVSEENTGNGGAVTADNPKN
EDEVAQNDMPQNAAGTDSSTPNHTPDPNMLAGNMENQATDAGESSQPANQPDMANAADGMQGDDPSAGG
QNAGNTAAQGANQAGNNQAAGSSDPIPASNPAPANGGSNFGRVDLANGVLIDGPSQNITLTHCKGDSCS
GNNFLDEEVQLKSEFEKLSDADKISNYKKDGKNDKFVGLVADSVQMKGINQYIIFYKPKPTSFARFRRS
ARSRRSLPAEMPLIPVNQADTLIVDGEAVSLTGHSGNIFAPEGNYRYLTYGAEKLPGGSYALRVQGEPA
KGEMLAGAAVYNGEVLHFHTENGRPYPTRGRFAAKVDFGSKSVDGIIDSGDDLHMGTQKFKAAIDGNGF
KGTWTENGSGDVSGKFYGPAGEEVAGKYSYRPTDAEKGGFGVFAGKKEQD >SEQ ID NO: 13 [NHBA mature]
CGGGGGGSPDVKSADTLSKPAAPVVSEKETEAKEDAPQAGSQGQGAPSAQGSQDMAAVSEENTGNGGAV
TADNPKNEDEVAQNDMPQNAAGTDSSTPNHTPDPNMLAGNMENQATDAGESSQPANQPDMANAADGMQG
DDPSAGGQNAGNTAAQGANQAGNNQAAGSSDPIPASNPAPANGGSNFGRVDLANGVLIDGPSQNITLTH
CKGDSCSGNNFLDEEVQLKSEFEKLSDADKISNYKKDGKNDKFVGLVADSVQMKGINQYIIFYKPKPTS
FARFRRSARSRRSLPAEMPLIPVNQADTLIVDGEAVSLTGHSGNIFAPEGNYRYLTYGAEKLPGGSYAL
RVQGEPAKGEMLAGAAVYNGEVLHFHTENGRPYPTRGRFAAKVDFGSKSVDGIIDSGDDLHMGTQKFKA
AIDGNGFKGTWTENGSGDVSGKFYGPAGEEVAGKYSYRPTDAEKGGEGVFAGKKEQD >SEQ ID NO: 14 [NMB1030, MC58]
MKKIIFAALAAAAISTASAATYKVDEYHANARFAIDHFNTSTNVGGFYGLTGSVEFDQAKRDGKIDITI
PIANLQSGSQHFTDHLKSADIFDAAQYPDIREVSTKENENGKKLVSVDGNLTMHGKTAPVKLKAEKFNC
YQSPMEKTEVCGGDFSTTIDRTKWGMDYLVNVGMTKSVRIDIQIEAAKQ >SEQ ID NO: 15 [NMB1030 fragment]
ATYKVDEYHANARFAIDHFNTSTNVGGFYGLTGSVEFDQAKRDGKIDITIPIANLQSGSQHFTDHLKSA
DIFDAAQYPDIREVSTKENENGKKLVSVDGNLTMHGKTAPVKLKAEKENCYQSPMEKTEVCGGDFSTTI
DRTKWGMDYLVNVGMTKSVRIDIQIEAAKQ >SEQ ID NO: 16 [NHBA fusion]
MASPDVKSADTLSKPAAPVVSEKETEAKEDAPQAGSQGQGAPSAQGGQDMAAVSEENTGNGGAAATDKP
KNEDEGAQNDMPQNAADTDSLTPNHTPASNMPAGNMENQAPDAGESEQPANQPDMANTADGMQGDDPSA
GGENAGNTAAQGTNQAENNQTAGSQNPASSTNPSATNSGGDFGRTNVGNSVVIDGPSQNITLTHCKGDS
CSGNNFLDEEVQLKSEFEKLSDADKISNYKKDGKNDGKNDKFVGLVADSVQMKGINQYIIFYKPKPTSF
ARFRRSARSRRSLPAEMPLIPVNQADTLIVDGEAVSLTGHSGNIFAPEGNYRYLTYGAEKLPGGSYALR
VQGEPSKGEMLAGTAVYNGEVLHFHTENGRPSPSRGRFAAKVDFGSKSVDGIIDSGDGLHMGTQKFKAA
IDGNGFKGTWTENGGGDVSGKFYGPAGEEVAGKYSYRPTDAEKGGEGVFAGKKEQDGSGGGGATYKVDE
YHANARFAIDHFNTSTNVGGFYGLTGSVEFDQAKRDGKIDITIPVANLQSGSQHFTDHLKSADIFDAAQ
YPDIREVSTKENENGKKLVSVDGNLTMHGKTAPVKLKAEKENCYQSPMAKTEVCGGDFSTTIDRTKWGV
DYLVNVGMTKSVRIDIQIEAAKQ >SEQ ID NO: 17 [NadA, MC58]
MSMKHFPSKVLTTAILATFCSGALAATSDDDVKKAATVAIVAAYNNGQEINGFKAGETIYDIGEDGTIT
QKDATAADVEADDFKGLGLKKVVTNLTKTVNENKQNVDAKVKAAESEIEKLTTKLADTDAALADTDAAL
DETTNALNKLGENITTFAEETKTNIVKIDEKLEAVADTVDKHAEAFNDIADSLDETNTKADEAVKTANE -continued

SEQUENCE LISTING

AKQTAEETKQNVDAKVKAAETAAGKAEAAAGTANTAADKAEAVAAKVTDIKADIATNKADIAKNSARID
SLDKNVANLRKETRQGLAEQAALSGLFQPYNVGRENVTAAVGGYKSESAVAIGTGERFTENFAAKAGVA
VGTSSGSSAAYHVGVNYEW

>SEQ ID NO: 18 [NadA]
LAATSDDDVKKAATVAIVAAYNNGQEINGFKAGETIYDIGEDGTITQKDATAADVEADDFKGLGLKKVV
TNLTKTVNENKQNVDAKVKAAESEIEKLTTKLADTDAALADTDAALDETTNALNKLGENITTFAEETKT
NIVKIDEKLEAVADTVDKHAEAFNDIADSLDETNTKADEAVKTANEAKQTAEETKQNVDAKVKAAETAA
GKAEAAAGTANTAADKAEAVAAKVTDIKADIATNKADIAKNSARIDSLDKNVANLRKETRQGLAEQAAL
SGLFQPYNVGRENVTAAVGGYKSESAVAIGTGFRFTENFAAKAGVAVGTSSGSSAAYHVGVNYEW

>SEQ ID NO: 19 [NadA fragment]
ATNDDDVKKAATVAIAAAYNNGQEINGFKAGETIYDIDEDGTITKKDATAADVEADDFKGLGLKKVVTN
LTKTVNENKQNVDAKVKAAESEIEKLTTKLADTDAALADTDAALDATTNALNKLGENITTFAEETKTNI
VKIDEKLEAVADTVDKHAEAFNDIADSLDETNTKADEAVKTANEAKQTAEETKQNVDAKVKAAETAAGK
AEAAAGTANTAADKAEAVAAKVTDIKADIATNKDNIAKKANSADVYTREESDSKEVRIDGLNATTEKLD
TRLASAEKSIADHDTRLNGLDKTVSDLRKETRQGLAEQAALSGLFQPYNVG >SEQ ID NO: 20 [NMB2091, MC58]
MKPKPHTVRTLIAAIFSLALSGCVSAVIGSAAVGAKSAVDRRTTGAQTDDNVMALRIETTARSYLRQNN
QTKGYTPQISVVGYNRHLLLLGQVATEGEKQFVGQTARSEQAAEGVYNYITVASLPRTAGDIAGDTWNT
SKVRATLLGISPATQARVKIVTYGNVTYVMGILTPEEQAQITQKVSTTVGVQKVITLYQNYVQR >SEQ ID NO: 21 [NMB2091]
SAVIGSAAVGAKSAVDRRTTGAQTDDNVMALRIETTARSYLRQNNQTKGYTPQISVVGYDRHLLLLGQV
ATEGEKQFVGQTARSEQAAEGVYNYITVASLPRTAGDIAGDTWNTSKVRATLLGISPATRARVKIVTYG
NVTYVMGILTPEEQAQITQKVSTTVGVQKVITLYQNYVQR >SEQ ID NO: 22 [linker]
GSGGGG >SEQ ID NO: 23 [linker]
GPDSDRLQQRR >SEQ ID NO: 24 [linker]
GSGPDSDRLQQRR >SEQ ID NO: 25 [linker]
GKGPDSDRLQQRR >SEQ ID NO: 26 [N-terminal sequence]
MGPDSDRLQQRR >SEQ ID NO: 27 [N-terminal sequence]
MAS >SEQ ID NO: 28 [linker]
LEHHHHHH >SEQ ID NO: 29 [fHbp fusion polypeptide]
MGPDSDRLQQRRVAADIGAGLADALTAPLDHKDKSLQSLILDQSVRKNEKLKLAAQGAEKTYGNGDSLN
TGKLKNDKVSREDFIRQIEVDGQLITLESGEFQIYKQDHSAVVALQIEKINNPDKIDSLINQRSELVSG
LGGEHTAFNQLPDGKAEYHGKAFSSDDAGGKLTYTIDFAAKQGHGKIEHLKTPEQNVELAAAELKADEK
SHAVILGDTRYGSEEKGTYHLALFGDRAQEIAGSATVKIGEKVHEIGIAGKQGSGGGGVAADIGTGLAD
ALTAPLDHKDKGLKSLTLEDSIPQNGTLTLSAQGAEKTFKAGDKDNSLNIGKLKNDKISREDEVQKIEV
DGQIITLASGEFQIYKQNHSAVVALQIEKINNPDKTDSLINQRSFLVSGLGGEHTAFNQLPGGKAEYHG
KAFSSDDPNGRLHYSIDETKKQGYGRIEHLKTLEQNVELAAAELKADEKSHAVILGDTRYGSEEKGTYH
LALFGDRAQEIAGSATVKIGEKVHEIGIAGKQGSGGGGVAADIGAGLADALTAPLDHKDKGLQSLILDQ
SVRKNEKLKLAAQGAEKTYGNGDSLNIGKLKNDKVSREDFIRQIEVDGQLITLESGEFQVYKQSHSALT
AFQTEQIQDSEHSGKMVAKRQFRIGDIAGEHTSFDKLPEGGRATYRGTAFGSDDAGGKLTYTIDFAAKQ
GNGKIEHLKSPELNVDLAAADIKPDGKRHAVISGSVLYNQAEKGSYSLGIFGGKAQEVAGSAEVKTVNG
IRHIGLAAKQ >SEQ ID NO: 30 [fHbp fusion polypeptide]
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSELVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDSIPQNGTLTLSAQGAEKTFKAGDKDNSLNIGKLKNDKISREDEVQKIEVDGQIITLASGEF
QIYKQNHSAVVALQIEKINNPDKTDSLINQRSELVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVRKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ -continued

SEQUENCE LISTING

>SEQ ID NO: 31 [fHbp fusion polypeptide, fH binding disrupted]
Where X at residue 240 is any amino acid other than E, X at residue 496 is any amino acid other than E, and X at residue 543 is any amino acid other than R.
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSELVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHXIGIAGKQGSGGGGVAADIGTGLADALTAPLDHKDKG
LKSLTLEDSIPQNGTLTLSAQGAEKTFKAGDKDNSLNIGKLKNDKISREDEVQKIEVDGQIITLASGEF
QIYKQNHSAVVALQIEKINNPDKTDSLINQRSELVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHXIGIAGKQGSGGGGVAADIGAGLADALTAPLDHKDKGLQSLILDQSVXKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 32 [FHbp fusion polypeptide, fH binding disrupted]
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSELVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHAIGIAGKQGSGGGGVAADIGTGLADALTAPLDHKDKG
LKSLTLEDSIPQNGTLTLSAQGAEKTFKAGDKDNSLNIGKLKNDKISREDEVQKIEVDGQIITLASGEF
QIYKQNHSAVVALQIEKINNPDKTDSLINQRSELVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHAIGIAGKQGSGGGGVAADIGAGLADALTAPLDHKDKGLQSLILDQSVSKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 33 [fHbp fusion polypeptide, stabilised]
Where X at residue 32 is any amino acid other than S, X at residue 123 is any amino acid other than L, X at residue 285 is any amino acid other than S, and X at residue 379 is any amino acid other than L.
VAADIGAGLADALTAPLDHKDKSLQSLILDQXVRKNEKLKLAAQGAEKTYGNGDSLNIGKLKNDKVSRF
DFIRQIEVDGQLITLESGEFQIYKQDHSAVVALQIEKINNPDKIDSLINQRSFXVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDXIPQNGTLTLSAQGAEKTFKAGDKDNSLNIGKLKNDKISREDEVQKIEVDGQIITLASGEF
QIYKQNHSAVVALQIEKINNPDKTDSLINQRSFXVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVRKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 34 [fHbp fusion polypeptide, stabilised]
VAADIGAGLADALTAPLDHKDKSLQSLTLDQVVRKNEKLKLAAQGAEKTYGNGDSLNIGKLKNDKVSRF
DFIRQIEVDGQLITLESGEFQIYKQDHSAVVALQIEKINNPDKIDSLINQRSERVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDVIPQNGTLTLSAQGAEKTFKAGDKDNSLNIGKLKNDKISREDEVQKIEVDGQIITLASGEF
QIYKQNHSAVVALQIEKINNPDKTDSLINQRSERVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVRKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 35 [fHbp fusion polypeptide, stabilised & R41]
Where X at residue 32 is any amino acid other thanS , X at residue 123 is any amino acid other than L, X at residue 285 is any amino acid other than S, X at residue 379 is any amino acid other than L, and X at residue 543 is any amino acid other than R.
VAADIGAGLADALTAPLDHKDKSLQSLILDQXVRKNEKLKLAAQGAEKTYGNGDSLNIGKLKNDKVSRF
DFIRQIEVDGQLITLESGEFQIYKQDHSAVVALQIEKINNPDKIDSLINQRSFXVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDXIPQNGTLTLSAQGAEKTFKAGDKDNSLNIGKLKNDKISREDEVQKIEVDGQIITLASGEF
QIYKQNHSAVVALQIEKINNPDKTDSLINQRSFXVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVXKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ -continued

SEQUENCE LISTING

>SEQ ID NO: 36 [fHbp fusion polypeptide, stabilised & R41S]
VAADIGAGLADALTAPLDHKDKSLQSLTLDQVVRKNEKLKLAAQGAEKTYGNGDSLNIGKLKNDKVSRF
DFIRQIEVDGQLITLESGEFQIYKQDHSAVVALQIEKINNPDKIDSLINQRSERVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDVIPQNGTLTLSAQGAEKTFKAGDKDNSLNIGKLKNDKISREDEVQKIEVDGQIITLASGEF
QIYKQNHSAVVALQIEKINNPDKTDSLINQRSERVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVSKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 37 [fHbp fusion polypeptide, stabilised, fH binding disrupted, & R41]
VAADIGAGLADALTAPLDHKDKSLQSLTLDQVVRKNEKLKLAAQGAEKTYGNGDSLNIGKLKNDKVSRF
DFIRQIEVDGQLITLESGEFQIYKQDHSAVVALQIEKINNPDKIDSLINQRSERVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHAIGIAGKQGSGGGGVAADIGTGLADALTAPLDHKDKG
LKSLTLEDVIPQNGTLTLSAQGAEKTFKAGDKDNSLNIGKLKNDKISREDEVQKIEVDGQIITLASGEF
QIYKQNHSAVVALQIEKINNPDKTDSLINQRSERVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHAIGIAGKQGSGGGGVAADIGAGLADALTAPLDHKDKGLQSLILDQSVSKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 38 [fHbp fusion polypeptide, stabilised, fH binding disrupted, & R41]
MGPDSDRLQQRRVAADIGAGLADALTAPLDHKDKSLQSLILDQVVRKNEKLKLAAQGAEKTYGNGDSLN
TGKLKNDKVSREDFIRQIEVDGQLITLESGEFQIYKQDHSAVVALQIEKINNPDKIDSLINQRSERVSG
LGGEHTAFNQLPDGKAEYHGKAFSSDDAGGKLTYTIDFAAKQGHGKIEHLKTPEQNVELAAAELKADEK
SHAVILGDTRYGSEEKGTYHLALFGDRAQEIAGSATVKIGEKVHAIGIAGKQGSGGGGVAADIGTGLAD
ALTAPLDHKDKGLKSLTLEDVIPQNGTLTLSAQGAEKTFKAGDKDNSLNIGKLKNDKISREDEVQKIEV
DGQIITLASGEFQIYKQNHSAVVALQIEKINNPDKTDSLINQRSFRVSGLGGEHTAFNQLPGGKAEYHG
KAFSSDDPNGRLHYSIDETKKQGYGRIEHLKTLEQNVELAAAELKADEKSHAVILGDTRYGSEEKGTYH
LALFGDRAQEIAGSATVKIGEKVHAIGIAGKQGSGGGGVAADIGAGLADALTAPLDHKDKGLQSLILDQ
SVSKNEKLKLAAQGAEKTYGNGDSLNIGKLKNDKVSREDFIRQIEVDGQLITLESGEFQVYKQSHSALT
AFQTEQIQDSEHSGKMVAKRQFRIGDIAGEHTSFDKLPEGGRATYRGTAFGSDDAGGKLTYTIDFAAKQ
GNGKIEHLKSPELNVDLAAADIKPDGKRHAVISGSVLYNQAEKGSYSLGIFGGKAQEVAGSAEVKTVNG
IRHIGLAAKQ >SEQ ID NO: 39 [fHbp fusion polypeptide, stabilised]
Where X at residue 123 is any amino acid other than L and X at residue 379 is any amino acid other than L.
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSFXVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDSIPQNGTLTLSAQGAEKTFKAGDKDNSLNIGKLKNDKISREDEVQKIEVDGQIITLASGEF
QIYKQNHSAVVALQIEKINNPDKTDSLINQRSFXVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVRKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 40 [fHbp fusion polypeptide, stabilised]
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSERVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDSIPQNGTLTLSAQGAEKTFKAGDKDNSLNIGKLKNDKISREDEVQKIEVDGQIITLASGEF
QIYKQNHSAVVALQIEKINNPDKTDSLINQRSERVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVRKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ >SEQ ID NO: 41 [fHbp fusion polypeptide, stabilised, R41S]
VAADIGAGLADALTAPLDHKDKSLQSLILDQSVRKNEKLKLAAQGAEKTYGNGDSLNIGKLKNDKVSRF
DFIRQIEVDGQLITLESGEFQIYKQDHSAVVALQIEKINNPDKIDSLINQRSERVSGLGGEHTAFNQLP
DGKAEYHGKAFSSDDAGGKLTYTIDFAAKQGHGKIEHLKTPEQNVELAAAELKADEKSHAVILGDTRYG
SEEKGTYHLALFGDRAQEIAGSATVKIGEKVHEIGIAGKQGSGGGGVAADIGTGLADALTAPLDHKDKG
LKSLTLEDSIPQNGTLTLSAQGAEKTFKAGDKDNSLNIGKLKNDKISREDEVQKIEVDGQIITLASGEF -continued

SEQUENCE LISTING

QIYKQNHSAVVALQIEKINNPDKTDSLINQRSERVSGLGGEHTAFNQLPGGKAEYHGKAFSSDDPNGRL
HYSIDETKKQGYGRIEHLKTLEQNVELAAAELKADEKSHAVILGDTRYGSEEKGTYHLALFGDRAQEIA
GSATVKIGEKVHEIGIAGKQGSGGGGVAADIGAGLADALTAPLDHKDKGLQSLILDQSVSKNEKLKLAA
QGAEKTYGNGDSLNIGKLKNDKVSREDFIRQIEVDGQLITLESGEFQVYKQSHSALTAFQTEQIQDSEH
SGKMVAKRQFRIGDIAGEHTSFDKLPEGGRATYRGTAFGSDDAGGKLTYTIDFAAKQGNGKIEHLKSPE
LNVDLAAADIKPDGKRHAVISGSVLYNQAEKGSYSLGIEGGKAQEVAGSAEVKTVNGIRHIGLAAKQ

The invention claimed is:

1. An immunogenic composition comprising a fusion polypeptide comprising all three of v1, v2 and v3 meningococcal fHbp, in combination with (i) a purified meningococcal NHBA polypeptide (ii) a purified meningococcal NadA polypeptide and (iii) meningococcal outer membrane vesicles (OMVs) prepared from meningococcal strain NZ98/254, wherein the fHbp fusion polypeptide has an amino acid sequence of formula $NH_2$-A-[-X-L]$_3$-B—COOH, L is an optional linker amino acid sequence, A is an optional N terminal amino acid sequence, and B is an optional C terminal amino acid sequence, wherein X1, X2 and X3 are the three of the meningococcal fHbp sequences in the order v2-v3-v1 from the N- to C-terminus, wherein the v1 fHbp sequence comprises a sequence with at least 90% sequence identity to SEQ ID NO: 7, wherein the v2 fHbp sequence comprises the sequence of SEQ ID NO: 8 but is modified to introduce a stabilizing substitution at S32 that is an amino acid that is not serine, and a stabilizing substitution at L123 that is an amino acid that is not leucine, and wherein the v3 fHbp sequence comprises the sequence of SEQ ID NO: 9 but is modified to introduce a stabilizing substitution at S32 that is an amino acid that is not serine, and a stabilizing substitution at L126 that is an amino acid that is not leucine.

2. The composition of claim 1, wherein:

(i) the meningococcal NHBA polypeptide comprises an amino acid sequence having 90% or more identity to SEQ ID NO: 12; and/or (ii) the meningococcal NadA polypeptide comprises an amino acid sequence having 90% or more identity to SEQ ID NO: 17.

3. The composition of claim 1, further comprising an aluminum hydroxide adjuvant.

4. The composition of claim 1, wherein the v2 meningococcal fHbp of SEQ ID NO:8 has the S32V and L123R mutations.

* * * * *

SEQUENCE LISTING

<160> NUMBER OF SEQ ID NOS: 44

<210> SEQ ID NO 1
<211> LENGTH: 274
<212> TYPE: PRT
<213> ORGANISM: Neisseria meningitidis

<400> SEQUENCE: 1

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln
```

<210> SEQ ID NO 2

-continued

<211> LENGTH: 273
<212> TYPE: PRT
<213> ORGANISM: Neisseria meningitidis

<400> SEQUENCE: 2

```
Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln
```

<210> SEQ ID NO 3
<211> LENGTH: 281
<212> TYPE: PRT
<213> ORGANISM: Neisseria meningitidis

<400> SEQUENCE: 3

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60
```

```
Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280


<210> SEQ ID NO 4
<211> LENGTH: 255
<212> TYPE: PRT
<213> ORGANISM: Neisseria meningitidis

<400> SEQUENCE: 4

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160
```

```
Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255


<210> SEQ ID NO 5
<211> LENGTH: 254
<212> TYPE: PRT
<213> ORGANISM: Neisseria meningitidis

<400> SEQUENCE: 5

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250


<210> SEQ ID NO 6
<211> LENGTH: 262
<212> TYPE: PRT
```

-continued

<213> ORGANISM: Neisseria meningitidis

<400> SEQUENCE: 6

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 7
<211> LENGTH: 248
<212> TYPE: PRT
<213> ORGANISM: Neisseria meningitidis

<400> SEQUENCE: 7

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His

```
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245


<210> SEQ ID NO 8
<211> LENGTH: 247
<212> TYPE: PRT
<213> ORGANISM: Neisseria meningitidis

<400> SEQUENCE: 8

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205
```

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 9
<211> LENGTH: 250
<212> TYPE: PRT
<213> ORGANISM: Neisseria meningitidis

<400> SEQUENCE: 9

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 10
<211> LENGTH: 776
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Met Gly Pro Asp Ser Asp Arg Leu Gln Gln Arg Arg Val Ala Ala Asp
1               5                   10                  15

-continued

```
Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Pro Asp Ser Asp Arg Leu Gln Gln Arg Arg
            260                 265                 270

Val Ala Ala Asp Ile Gly Thr Gly Leu Ala Asp Ala Leu Thr Ala Pro
        275                 280                 285

Leu Asp His Lys Asp Lys Gly Leu Lys Ser Leu Thr Leu Glu Asp Ser
    290                 295                 300

Ile Pro Gln Asn Gly Thr Leu Thr Leu Ser Ala Gln Gly Ala Glu Lys
305                 310                 315                 320

Thr Phe Lys Ala Gly Asp Lys Asp Asn Ser Leu Asn Thr Gly Lys Leu
                325                 330                 335

Lys Asn Asp Lys Ile Ser Arg Phe Asp Phe Val Gln Lys Ile Glu Val
            340                 345                 350

Asp Gly Gln Thr Ile Thr Leu Ala Ser Gly Glu Phe Gln Ile Tyr Lys
        355                 360                 365

Gln Asn His Ser Ala Val Val Ala Leu Gln Ile Glu Lys Ile Asn Asn
    370                 375                 380

Pro Asp Lys Thr Asp Ser Leu Ile Asn Gln Arg Ser Phe Leu Val Ser
385                 390                 395                 400

Gly Leu Gly Gly Glu His Thr Ala Phe Asn Gln Leu Pro Gly Gly Lys
                405                 410                 415

Ala Glu Tyr His Gly Lys Ala Phe Ser Ser Asp Asp Pro Asn Gly Arg
            420                 425                 430
```

-continued

```
Leu His Tyr Ser Ile Asp Phe Thr Lys Lys Gln Gly Tyr Gly Arg Ile
        435                 440                 445

Glu His Leu Lys Thr Leu Glu Gln Asn Val Glu Leu Ala Ala Ala Glu
    450                 455                 460

Leu Lys Ala Asp Glu Lys Ser His Ala Val Ile Leu Gly Asp Thr Arg
465                 470                 475                 480

Tyr Gly Ser Glu Glu Lys Gly Thr Tyr His Leu Ala Leu Phe Gly Asp
                485                 490                 495

Arg Ala Gln Glu Ile Ala Gly Ser Ala Thr Val Lys Ile Gly Glu Lys
            500                 505                 510

Val His Glu Ile Gly Ile Ala Gly Lys Gln Gly Ser Gly Gly Gly Gly
        515                 520                 525

Val Ala Ala Asp Ile Gly Ala Gly Leu Ala Asp Ala Leu Thr Ala Pro
    530                 535                 540

Leu Asp His Lys Asp Lys Gly Leu Gln Ser Leu Thr Leu Asp Gln Ser
545                 550                 555                 560

Val Arg Lys Asn Glu Lys Leu Lys Leu Ala Ala Gln Gly Ala Glu Lys
                565                 570                 575

Thr Tyr Gly Asn Gly Asp Ser Leu Asn Thr Gly Lys Leu Lys Asn Asp
            580                 585                 590

Lys Val Ser Arg Phe Asp Phe Ile Arg Gln Ile Glu Val Asp Gly Gln
        595                 600                 605

Leu Ile Thr Leu Glu Ser Gly Glu Phe Gln Val Tyr Lys Gln Ser His
    610                 615                 620

Ser Ala Leu Thr Ala Phe Gln Thr Glu Gln Ile Gln Asp Ser Glu His
625                 630                 635                 640

Ser Gly Lys Met Val Ala Lys Arg Gln Phe Arg Ile Gly Asp Ile Ala
                645                 650                 655

Gly Glu His Thr Ser Phe Asp Lys Leu Pro Glu Gly Gly Arg Ala Thr
            660                 665                 670

Tyr Arg Gly Thr Ala Phe Gly Ser Asp Asp Ala Gly Gly Lys Leu Thr
        675                 680                 685

Tyr Thr Ile Asp Phe Ala Ala Lys Gln Gly Asn Gly Lys Ile Glu His
    690                 695                 700

Leu Lys Ser Pro Glu Leu Asn Val Asp Leu Ala Ala Ala Asp Ile Lys
705                 710                 715                 720

Pro Asp Gly Lys Arg His Ala Val Ile Ser Gly Ser Val Leu Tyr Asn
                725                 730                 735

Gln Ala Glu Lys Gly Ser Tyr Ser Leu Gly Ile Phe Gly Gly Lys Ala
            740                 745                 750

Gln Glu Val Ala Gly Ser Ala Glu Val Lys Thr Val Asn Gly Ile Arg
        755                 760                 765

His Ile Gly Leu Ala Ala Lys Gln
    770                 775


<210> SEQ ID NO 11
<211> LENGTH: 488
<212> TYPE: PRT
<213> ORGANISM: Neisseria meningitidis

<400> SEQUENCE: 11

Met Phe Lys Arg Ser Val Ile Ala Met Ala Cys Ile Phe Ala Leu Ser
1               5                   10                  15

Ala Cys Gly Gly Gly Gly Gly Gly Ser Pro Asp Val Lys Ser Ala Asp
            20                  25                  30
```

-continued

```
Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445
```

```
Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485


<210> SEQ ID NO 12
<211> LENGTH: 464
<212> TYPE: PRT
<213> ORGANISM: Neisseria meningitidis

<400> SEQUENCE: 12

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
            20                  25                  30

Gly Ser Gln Gly Gln Gly Ala Pro Ser Ala Gln Gly Ser Gln Asp Met
        35                  40                  45

Ala Ala Val Ser Glu Glu Asn Thr Gly Asn Gly Gly Ala Val Thr Ala
    50                  55                  60

Asp Asn Pro Lys Asn Glu Asp Glu Val Ala Gln Asn Asp Met Pro Gln
65                  70                  75                  80

Asn Ala Ala Gly Thr Asp Ser Ser Thr Pro Asn His Thr Pro Asp Pro
                85                  90                  95

Asn Met Leu Ala Gly Asn Met Glu Asn Gln Ala Thr Asp Ala Gly Glu
            100                 105                 110

Ser Ser Gln Pro Ala Asn Gln Pro Asp Met Ala Asn Ala Ala Asp Gly
        115                 120                 125

Met Gln Gly Asp Asp Pro Ser Ala Gly Gly Gln Asn Ala Gly Asn Thr
    130                 135                 140

Ala Ala Gln Gly Ala Asn Gln Ala Gly Asn Asn Gln Ala Ala Gly Ser
145                 150                 155                 160

Ser Asp Pro Ile Pro Ala Ser Asn Pro Ala Pro Ala Asn Gly Gly Ser
                165                 170                 175

Asn Phe Gly Arg Val Asp Leu Ala Asn Gly Val Leu Ile Asp Gly Pro
            180                 185                 190

Ser Gln Asn Ile Thr Leu Thr His Cys Lys Gly Asp Ser Cys Ser Gly
        195                 200                 205

Asn Asn Phe Leu Asp Glu Glu Val Gln Leu Lys Ser Glu Phe Glu Lys
    210                 215                 220

Leu Ser Asp Ala Asp Lys Ile Ser Asn Tyr Lys Lys Asp Gly Lys Asn
225                 230                 235                 240

Asp Lys Phe Val Gly Leu Val Ala Asp Ser Val Gln Met Lys Gly Ile
                245                 250                 255

Asn Gln Tyr Ile Ile Phe Tyr Lys Pro Lys Pro Thr Ser Phe Ala Arg
            260                 265                 270

Phe Arg Arg Ser Ala Arg Ser Arg Arg Ser Leu Pro Ala Glu Met Pro
        275                 280                 285

Leu Ile Pro Val Asn Gln Ala Asp Thr Leu Ile Val Asp Gly Glu Ala
    290                 295                 300

Val Ser Leu Thr Gly His Ser Gly Asn Ile Phe Ala Pro Glu Gly Asn
305                 310                 315                 320

Tyr Arg Tyr Leu Thr Tyr Gly Ala Glu Lys Leu Pro Gly Gly Ser Tyr
                325                 330                 335
```

Ala Leu Arg Val Gln Gly Glu Pro Ala Lys Gly Glu Met Leu Ala Gly
            340                 345                 350

Ala Ala Val Tyr Asn Gly Glu Val Leu His Phe His Thr Glu Asn Gly
        355                 360                 365

Arg Pro Tyr Pro Thr Arg Gly Arg Phe Ala Ala Lys Val Asp Phe Gly
    370                 375                 380

Ser Lys Ser Val Asp Gly Ile Ile Asp Ser Gly Asp Asp Leu His Met
385                 390                 395                 400

Gly Thr Gln Lys Phe Lys Ala Ala Ile Asp Gly Asn Gly Phe Lys Gly
                405                 410                 415

Thr Trp Thr Glu Asn Gly Ser Gly Asp Val Ser Gly Lys Phe Tyr Gly
            420                 425                 430

Pro Ala Gly Glu Glu Val Ala Gly Lys Tyr Ser Tyr Arg Pro Thr Asp
        435                 440                 445

Ala Glu Lys Gly Gly Phe Gly Val Phe Ala Gly Lys Lys Glu Gln Asp
    450                 455                 460

<210> SEQ ID NO 13
<211> LENGTH: 471
<212> TYPE: PRT
<213> ORGANISM: Neisseria meningitidis

<400> SEQUENCE: 13

Cys Gly Gly Gly Gly Gly Gly Ser Pro Asp Val Lys Ser Ala Asp Thr
1               5                   10                  15

Leu Ser Lys Pro Ala Ala Pro Val Val Ser Glu Lys Glu Thr Glu Ala
            20                  25                  30

Lys Glu Asp Ala Pro Gln Ala Gly Ser Gln Gly Gln Gly Ala Pro Ser
        35                  40                  45

Ala Gln Gly Ser Gln Asp Met Ala Ala Val Ser Glu Glu Asn Thr Gly
    50                  55                  60

Asn Gly Gly Ala Val Thr Ala Asp Asn Pro Lys Asn Glu Asp Glu Val
65                  70                  75                  80

Ala Gln Asn Asp Met Pro Gln Asn Ala Ala Gly Thr Asp Ser Ser Thr
                85                  90                  95

Pro Asn His Thr Pro Asp Pro Asn Met Leu Ala Gly Asn Met Glu Asn
            100                 105                 110

Gln Ala Thr Asp Ala Gly Glu Ser Ser Gln Pro Ala Asn Gln Pro Asp
        115                 120                 125

Met Ala Asn Ala Ala Asp Gly Met Gln Gly Asp Asp Pro Ser Ala Gly
    130                 135                 140

Gly Gln Asn Ala Gly Asn Thr Ala Ala Gln Gly Ala Asn Gln Ala Gly
145                 150                 155                 160

Asn Asn Gln Ala Ala Gly Ser Ser Asp Pro Ile Pro Ala Ser Asn Pro
                165                 170                 175

Ala Pro Ala Asn Gly Gly Ser Asn Phe Gly Arg Val Asp Leu Ala Asn
            180                 185                 190

Gly Val Leu Ile Asp Gly Pro Ser Gln Asn Ile Thr Leu Thr His Cys
        195                 200                 205

Lys Gly Asp Ser Cys Ser Gly Asn Asn Phe Leu Asp Glu Glu Val Gln
    210                 215                 220

Leu Lys Ser Glu Phe Glu Lys Leu Ser Asp Ala Asp Lys Ile Ser Asn
225                 230                 235                 240

Tyr Lys Lys Asp Gly Lys Asn Asp Lys Phe Val Gly Leu Val Ala Asp

-continued

```
                245                 250                 255

Ser Val Gln Met Lys Gly Ile Asn Gln Tyr Ile Ile Phe Tyr Lys Pro
            260                 265                 270

Lys Pro Thr Ser Phe Ala Arg Phe Arg Arg Ser Ala Arg Ser Arg Arg
        275                 280                 285

Ser Leu Pro Ala Glu Met Pro Leu Ile Pro Val Asn Gln Ala Asp Thr
    290                 295                 300

Leu Ile Val Asp Gly Glu Ala Val Ser Leu Thr Gly His Ser Gly Asn
305                 310                 315                 320

Ile Phe Ala Pro Glu Gly Asn Tyr Arg Tyr Leu Thr Tyr Gly Ala Glu
                325                 330                 335

Lys Leu Pro Gly Gly Ser Tyr Ala Leu Arg Val Gln Gly Glu Pro Ala
            340                 345                 350

Lys Gly Glu Met Leu Ala Gly Ala Ala Val Tyr Asn Gly Glu Val Leu
        355                 360                 365

His Phe His Thr Glu Asn Gly Arg Pro Tyr Pro Thr Arg Gly Arg Phe
    370                 375                 380

Ala Ala Lys Val Asp Phe Gly Ser Lys Ser Val Asp Gly Ile Ile Asp
385                 390                 395                 400

Ser Gly Asp Asp Leu His Met Gly Thr Gln Lys Phe Lys Ala Ala Ile
                405                 410                 415

Asp Gly Asn Gly Phe Lys Gly Thr Trp Thr Glu Asn Gly Ser Gly Asp
            420                 425                 430

Val Ser Gly Lys Phe Tyr Gly Pro Ala Gly Glu Glu Val Ala Gly Lys
        435                 440                 445

Tyr Ser Tyr Arg Pro Thr Asp Ala Glu Lys Gly Gly Phe Gly Val Phe
    450                 455                 460

Ala Gly Lys Lys Glu Gln Asp
465                 470


<210> SEQ ID NO 14
<211> LENGTH: 187
<212> TYPE: PRT
<213> ORGANISM: Neisseria meningitidis

<400> SEQUENCE: 14

Met Lys Lys Ile Ile Phe Ala Ala Leu Ala Ala Ala Ala Ile Ser Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Ile Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Glu
    130                 135                 140
```

Lys Thr Glu Val Cys Gly Gly Asp Phe Ser Thr Thr Ile Asp Arg Thr
145 150 155 160

Lys Trp Gly Met Asp Tyr Leu Val Asn Val Gly Met Thr Lys Ser Val
165 170 175

Arg Ile Asp Ile Gln Ile Glu Ala Ala Lys Gln
180 185

<210> SEQ ID NO 15
<211> LENGTH: 168
<212> TYPE: PRT
<213> ORGANISM: Neisseria meningitidis

<400> SEQUENCE: 15

Ala Thr Tyr Lys Val Asp Glu Tyr His Ala Asn Ala Arg Phe Ala Ile
1 5 10 15

Asp His Phe Asn Thr Ser Thr Asn Val Gly Gly Phe Tyr Gly Leu Thr
20 25 30

Gly Ser Val Glu Phe Asp Gln Ala Lys Arg Asp Gly Lys Ile Asp Ile
35 40 45

Thr Ile Pro Ile Ala Asn Leu Gln Ser Gly Ser Gln His Phe Thr Asp
50 55 60

His Leu Lys Ser Ala Asp Ile Phe Asp Ala Ala Gln Tyr Pro Asp Ile
65 70 75 80

Arg Phe Val Ser Thr Lys Phe Asn Phe Asn Gly Lys Lys Leu Val Ser
85 90 95

Val Asp Gly Asn Leu Thr Met His Gly Lys Thr Ala Pro Val Lys Leu
100 105 110

Lys Ala Glu Lys Phe Asn Cys Tyr Gln Ser Pro Met Glu Lys Thr Glu
115 120 125

Val Cys Gly Gly Asp Phe Ser Thr Thr Ile Asp Arg Thr Lys Trp Gly
130 135 140

Met Asp Tyr Leu Val Asn Val Gly Met Thr Lys Ser Val Arg Ile Asp
145 150 155 160

Ile Gln Ile Glu Ala Ala Lys Gln
165

<210> SEQ ID NO 16
<211> LENGTH: 644
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Met Ala Ser Pro Asp Val Lys Ser Ala Asp Thr Leu Ser Lys Pro Ala
1 5 10 15

Ala Pro Val Val Ser Glu Lys Glu Thr Glu Ala Lys Glu Asp Ala Pro
20 25 30

Gln Ala Gly Ser Gln Gly Gln Gly Ala Pro Ser Ala Gln Gly Gly Gln
35 40 45

Asp Met Ala Ala Val Ser Glu Glu Asn Thr Gly Asn Gly Gly Ala Ala
50 55 60

Ala Thr Asp Lys Pro Lys Asn Glu Asp Glu Gly Ala Gln Asn Asp Met
65 70 75 80

Pro Gln Asn Ala Ala Asp Thr Asp Ser Leu Thr Pro Asn His Thr Pro
85 90 95

-continued

```
Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510
```

```
Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
    530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
    610                 615                 620

Val Asn Val Gly Met Thr Lys Ser Val Arg Ile Asp Ile Gln Ile Glu
625                 630                 635                 640

Ala Ala Lys Gln


<210> SEQ ID NO 17
<211> LENGTH: 364
<212> TYPE: PRT
<213> ORGANISM: Neisseria meningitidis

<400> SEQUENCE: 17

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
    50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Ala Gly Thr Ala
225                 230                 235                 240
```

```
Asn Thr Ala Ala Asp Lys Ala Glu Ala Val Ala Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360


<210> SEQ ID NO 18
<211> LENGTH: 341
<212> TYPE: PRT
<213> ORGANISM: Neisseria meningitidis

<400> SEQUENCE: 18

Leu Ala Ala Thr Ser Asp Asp Asp Val Lys Lys Ala Ala Thr Val Ala
1               5                   10                  15

Ile Val Ala Ala Tyr Asn Asn Gly Gln Glu Ile Asn Gly Phe Lys Ala
            20                  25                  30

Gly Glu Thr Ile Tyr Asp Ile Gly Glu Asp Gly Thr Ile Thr Gln Lys
        35                  40                  45

Asp Ala Thr Ala Ala Asp Val Glu Ala Asp Asp Phe Lys Gly Leu Gly
    50                  55                  60

Leu Lys Lys Val Val Thr Asn Leu Thr Lys Thr Val Asn Glu Asn Lys
65                  70                  75                  80

Gln Asn Val Asp Ala Lys Val Lys Ala Ala Glu Ser Glu Ile Glu Lys
                85                  90                  95

Leu Thr Thr Lys Leu Ala Asp Thr Asp Ala Ala Leu Ala Asp Thr Asp
            100                 105                 110

Ala Ala Leu Asp Glu Thr Thr Asn Ala Leu Asn Lys Leu Gly Glu Asn
        115                 120                 125

Ile Thr Thr Phe Ala Glu Glu Thr Lys Thr Asn Ile Val Lys Ile Asp
    130                 135                 140

Glu Lys Leu Glu Ala Val Ala Asp Thr Val Asp Lys His Ala Glu Ala
145                 150                 155                 160

Phe Asn Asp Ile Ala Asp Ser Leu Asp Glu Thr Asn Thr Lys Ala Asp
                165                 170                 175

Glu Ala Val Lys Thr Ala Asn Glu Ala Lys Gln Thr Ala Glu Glu Thr
            180                 185                 190

Lys Gln Asn Val Asp Ala Lys Val Lys Ala Ala Glu Thr Ala Ala Gly
        195                 200                 205

Lys Ala Glu Ala Ala Ala Gly Thr Ala Asn Thr Ala Ala Asp Lys Ala
    210                 215                 220

Glu Ala Val Ala Ala Lys Val Thr Asp Ile Lys Ala Asp Ile Ala Thr
225                 230                 235                 240

Asn Lys Ala Asp Ile Ala Lys Asn Ser Ala Arg Ile Asp Ser Leu Asp
                245                 250                 255
```

```
Lys Asn Val Ala Asn Leu Arg Lys Glu Thr Arg Gln Gly Leu Ala Glu
            260                 265                 270

Gln Ala Ala Leu Ser Gly Leu Phe Gln Pro Tyr Asn Val Gly Arg Phe
        275                 280                 285

Asn Val Thr Ala Ala Val Gly Gly Tyr Lys Ser Glu Ser Ala Val Ala
    290                 295                 300

Ile Gly Thr Gly Phe Arg Phe Thr Glu Asn Phe Ala Ala Lys Ala Gly
305                 310                 315                 320

Val Ala Val Gly Thr Ser Ser Gly Ser Ser Ala Ala Tyr His Val Gly
                325                 330                 335

Val Asn Tyr Glu Trp
            340


<210> SEQ ID NO 19
<211> LENGTH: 327
<212> TYPE: PRT
<213> ORGANISM: Neisseria meningitidis

<400> SEQUENCE: 19

Ala Thr Asn Asp Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
```

```
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325


<210> SEQ ID NO 20
<211> LENGTH: 202
<212> TYPE: PRT
<213> ORGANISM: Neisseria meningitidis

<400> SEQUENCE: 20

Met Lys Pro Lys Pro His Thr Val Arg Thr Leu Ile Ala Ala Ile Phe
1               5                   10                  15

Ser Leu Ala Leu Ser Gly Cys Val Ser Ala Val Ile Gly Ser Ala Ala
            20                  25                  30

Val Gly Ala Lys Ser Ala Val Asp Arg Arg Thr Thr Gly Ala Gln Thr
        35                  40                  45

Asp Asp Asn Val Met Ala Leu Arg Ile Glu Thr Thr Ala Arg Ser Tyr
    50                  55                  60

Leu Arg Gln Asn Asn Gln Thr Lys Gly Tyr Thr Pro Gln Ile Ser Val
65                  70                  75                  80

Val Gly Tyr Asn Arg His Leu Leu Leu Leu Gly Gln Val Ala Thr Glu
                85                  90                  95

Gly Glu Lys Gln Phe Val Gly Gln Ile Ala Arg Ser Glu Gln Ala Ala
            100                 105                 110

Glu Gly Val Tyr Asn Tyr Ile Thr Val Ala Ser Leu Pro Arg Thr Ala
        115                 120                 125

Gly Asp Ile Ala Gly Asp Thr Trp Asn Thr Ser Lys Val Arg Ala Thr
    130                 135                 140

Leu Leu Gly Ile Ser Pro Ala Thr Gln Ala Arg Val Lys Ile Val Thr
145                 150                 155                 160

Tyr Gly Asn Val Thr Tyr Val Met Gly Ile Leu Thr Pro Glu Glu Gln
                165                 170                 175

Ala Gln Ile Thr Gln Lys Val Ser Thr Thr Val Gly Val Gln Lys Val
            180                 185                 190

Ile Thr Leu Tyr Gln Asn Tyr Val Gln Arg
        195                 200


<210> SEQ ID NO 21
<211> LENGTH: 178
<212> TYPE: PRT
<213> ORGANISM: Neisseria meningitidis

<400> SEQUENCE: 21

Ser Ala Val Ile Gly Ser Ala Ala Val Gly Ala Lys Ser Ala Val Asp
1               5                   10                  15

Arg Arg Thr Thr Gly Ala Gln Thr Asp Asp Asn Val Met Ala Leu Arg
            20                  25                  30

Ile Glu Thr Thr Ala Arg Ser Tyr Leu Arg Gln Asn Asn Gln Thr Lys
        35                  40                  45

Gly Tyr Thr Pro Gln Ile Ser Val Val Gly Tyr Asp Arg His Leu Leu
    50                  55                  60

Leu Leu Gly Gln Val Ala Thr Glu Gly Glu Lys Gln Phe Val Gly Gln
```

```
65                  70                  75                  80

Ile Ala Arg Ser Glu Gln Ala Ala Glu Gly Val Tyr Asn Tyr Ile Thr
                85                  90                  95

Val Ala Ser Leu Pro Arg Thr Ala Gly Asp Ile Ala Gly Asp Thr Trp
            100                 105                 110

Asn Thr Ser Lys Val Arg Ala Thr Leu Leu Gly Ile Ser Pro Ala Thr
        115                 120                 125

Arg Ala Arg Val Lys Ile Val Thr Tyr Gly Asn Val Thr Tyr Val Met
    130                 135                 140

Gly Ile Leu Thr Pro Glu Glu Gln Ala Gln Ile Thr Gln Lys Val Ser
145                 150                 155                 160

Thr Thr Val Gly Val Gln Lys Val Ile Thr Leu Tyr Gln Asn Tyr Val
                165                 170                 175

Gln Arg


<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ser Gly Gly Gly Gly
1               5


<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Pro Asp Ser Asp Arg Leu Gln Gln Arg Arg
1               5                   10


<210> SEQ ID NO 24
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Ser Gly Pro Asp Ser Asp Arg Leu Gln Gln Arg Arg
1               5                   10


<210> SEQ ID NO 25
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25
```

```
Gly Lys Gly Pro Asp Ser Asp Arg Leu Gln Gln Arg Arg
1               5                   10


<210> SEQ ID NO 26
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Met Gly Pro Asp Ser Asp Arg Leu Gln Gln Arg Arg
1               5                   10


<210> SEQ ID NO 27
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Met Ala Ser
1


<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Leu Glu His His His His His His
1               5


<210> SEQ ID NO 29
<211> LENGTH: 769
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
```

-continued

```
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Gly Val Ala Ala Asp Ile Gly Thr
            260                 265                 270

Gly Leu Ala Asp Ala Leu Thr Ala Pro Leu Asp His Lys Asp Lys Gly
        275                 280                 285

Leu Lys Ser Leu Thr Leu Glu Asp Ser Ile Pro Gln Asn Gly Thr Leu
    290                 295                 300

Thr Leu Ser Ala Gln Gly Ala Glu Lys Thr Phe Lys Ala Gly Asp Lys
305                 310                 315                 320

Asp Asn Ser Leu Asn Thr Gly Lys Leu Lys Asn Asp Lys Ile Ser Arg
                325                 330                 335

Phe Asp Phe Val Gln Lys Ile Glu Val Asp Gly Gln Thr Ile Thr Leu
            340                 345                 350

Ala Ser Gly Glu Phe Gln Ile Tyr Lys Gln Asn His Ser Ala Val Val
        355                 360                 365

Ala Leu Gln Ile Glu Lys Ile Asn Asn Pro Asp Lys Thr Asp Ser Leu
    370                 375                 380

Ile Asn Gln Arg Ser Phe Leu Val Ser Gly Leu Gly Gly Glu His Thr
385                 390                 395                 400

Ala Phe Asn Gln Leu Pro Gly Gly Lys Ala Glu Tyr His Gly Lys Ala
                405                 410                 415

Phe Ser Ser Asp Asp Pro Asn Gly Arg Leu His Tyr Ser Ile Asp Phe
            420                 425                 430

Thr Lys Lys Gln Gly Tyr Gly Arg Ile Glu His Leu Lys Thr Leu Glu
        435                 440                 445

Gln Asn Val Glu Leu Ala Ala Ala Glu Leu Lys Ala Asp Glu Lys Ser
    450                 455                 460

His Ala Val Ile Leu Gly Asp Thr Arg Tyr Gly Ser Glu Glu Lys Gly
465                 470                 475                 480

Thr Tyr His Leu Ala Leu Phe Gly Asp Arg Ala Gln Glu Ile Ala Gly
                485                 490                 495

Ser Ala Thr Val Lys Ile Gly Glu Lys Val His Glu Ile Gly Ile Ala
            500                 505                 510

Gly Lys Gln Gly Ser Gly Gly Gly Gly Val Ala Ala Asp Ile Gly Ala
        515                 520                 525
```

```
Gly Leu Ala Asp Ala Leu Thr Ala Pro Leu Asp His Lys Asp Lys Gly
    530                 535                 540

Leu Gln Ser Leu Thr Leu Asp Gln Ser Val Arg Lys Asn Glu Lys Leu
545                 550                 555                 560

Lys Leu Ala Ala Gln Gly Ala Glu Lys Thr Tyr Gly Asn Gly Asp Ser
                565                 570                 575

Leu Asn Thr Gly Lys Leu Lys Asn Asp Lys Val Ser Arg Phe Asp Phe
            580                 585                 590

Ile Arg Gln Ile Glu Val Asp Gly Gln Leu Ile Thr Leu Glu Ser Gly
        595                 600                 605

Glu Phe Gln Val Tyr Lys Gln Ser His Ser Ala Leu Thr Ala Phe Gln
    610                 615                 620

Thr Glu Gln Ile Gln Asp Ser Glu His Ser Gly Lys Met Val Ala Lys
625                 630                 635                 640

Arg Gln Phe Arg Ile Gly Asp Ile Ala Gly Glu His Thr Ser Phe Asp
                645                 650                 655

Lys Leu Pro Glu Gly Gly Arg Ala Thr Tyr Arg Gly Thr Ala Phe Gly
            660                 665                 670

Ser Asp Asp Ala Gly Gly Lys Leu Thr Tyr Thr Ile Asp Phe Ala Ala
        675                 680                 685

Lys Gln Gly Asn Gly Lys Ile Glu His Leu Lys Ser Pro Glu Leu Asn
    690                 695                 700

Val Asp Leu Ala Ala Ala Asp Ile Lys Pro Asp Gly Lys Arg His Ala
705                 710                 715                 720

Val Ile Ser Gly Ser Val Leu Tyr Asn Gln Ala Glu Lys Gly Ser Tyr
                725                 730                 735

Ser Leu Gly Ile Phe Gly Gly Lys Ala Gln Glu Val Ala Gly Ser Ala
            740                 745                 750

Glu Val Lys Thr Val Asn Gly Ile Arg His Ile Gly Leu Ala Ala Lys
        755                 760                 765

Gln


<210> SEQ ID NO 30
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
```

-continued

```
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Ser Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Leu Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525
```

Lys Asp Lys Gly Leu Gln Ser Leu Thr Leu Asp Gln Ser Val Arg Lys
530 535 540

Asn Glu Lys Leu Lys Leu Ala Ala Gln Gly Ala Glu Lys Thr Tyr Gly
545 550 555 560

Asn Gly Asp Ser Leu Asn Thr Gly Lys Leu Lys Asn Asp Lys Val Ser
565 570 575

Arg Phe Asp Phe Ile Arg Gln Ile Glu Val Asp Gly Gln Leu Ile Thr
580 585 590

Leu Glu Ser Gly Glu Phe Gln Val Tyr Lys Gln Ser His Ser Ala Leu
595 600 605

Thr Ala Phe Gln Thr Glu Gln Ile Gln Asp Ser Glu His Ser Gly Lys
610 615 620

Met Val Ala Lys Arg Gln Phe Arg Ile Gly Asp Ile Ala Gly Glu His
625 630 635 640

Thr Ser Phe Asp Lys Leu Pro Glu Gly Gly Arg Ala Thr Tyr Arg Gly
645 650 655

Thr Ala Phe Gly Ser Asp Asp Ala Gly Gly Lys Leu Thr Tyr Thr Ile
660 665 670

Asp Phe Ala Ala Lys Gln Gly Asn Gly Lys Ile Glu His Leu Lys Ser
675 680 685

Pro Glu Leu Asn Val Asp Leu Ala Ala Ala Asp Ile Lys Pro Asp Gly
690 695 700

Lys Arg His Ala Val Ile Ser Gly Ser Val Leu Tyr Asn Gln Ala Glu
705 710 715 720

Lys Gly Ser Tyr Ser Leu Gly Ile Phe Gly Gly Lys Ala Gln Glu Val
725 730 735

Ala Gly Ser Ala Glu Val Lys Thr Val Asn Gly Ile Arg His Ile Gly
740 745 750

Leu Ala Ala Lys Gln
755

<210> SEQ ID NO 31
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (240)..(240)
<223> OTHER INFORMATION: Any amino acid except Glu
<220> FEATURE:
<221> NAME/KEY: MOD_RES
<222> LOCATION: (496)..(496)
<223> OTHER INFORMATION: Any amino acid except Glu
<220> FEATURE:
<221> NAME/KEY: MOD_RES
<222> LOCATION: (543)..(543)
<223> OTHER INFORMATION: Any amino acid except Arg

<400> SEQUENCE: 31

Val Ala Ala Asp Ile Gly Ala Gly Leu Ala Asp Ala Leu Thr Ala Pro
1 5 10 15

Leu Asp His Lys Asp Lys Ser Leu Gln Ser Leu Thr Leu Asp Gln Ser
20 25 30

Val Arg Lys Asn Glu Lys Leu Lys Leu Ala Ala Gln Gly Ala Glu Lys
35 40 45

```
Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Xaa
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Ser Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Leu Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
```

```
465                 470                 475                 480

Glu Ile Ala Gly Ser Ala Thr Val Lys Ile Gly Glu Lys Val His Xaa
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Xaa Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
            740                 745                 750

Leu Ala Ala Lys Gln
        755
```

<210> SEQ ID NO 32
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60
```

```
Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Ala
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Ser Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Leu Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480
```

Glu Ile Ala Gly Ser Ala Thr Val Lys Ile Gly Glu Lys Val His Ala
485 490 495

Ile Gly Ile Ala Gly Lys Gln Gly Ser Gly Gly Gly Gly Val Ala Ala
500 505 510

Asp Ile Gly Ala Gly Leu Ala Asp Ala Leu Thr Ala Pro Leu Asp His
515 520 525

Lys Asp Lys Gly Leu Gln Ser Leu Thr Leu Asp Gln Ser Val Ser Lys
530 535 540

Asn Glu Lys Leu Lys Leu Ala Ala Gln Gly Ala Glu Lys Thr Tyr Gly
545 550 555 560

Asn Gly Asp Ser Leu Asn Thr Gly Lys Leu Lys Asn Asp Lys Val Ser
565 570 575

Arg Phe Asp Phe Ile Arg Gln Ile Glu Val Asp Gly Gln Leu Ile Thr
580 585 590

Leu Glu Ser Gly Glu Phe Gln Val Tyr Lys Gln Ser His Ser Ala Leu
595 600 605

Thr Ala Phe Gln Thr Glu Gln Ile Gln Asp Ser Glu His Ser Gly Lys
610 615 620

Met Val Ala Lys Arg Gln Phe Arg Ile Gly Asp Ile Ala Gly Glu His
625 630 635 640

Thr Ser Phe Asp Lys Leu Pro Glu Gly Gly Arg Ala Thr Tyr Arg Gly
645 650 655

Thr Ala Phe Gly Ser Asp Asp Ala Gly Gly Lys Leu Thr Tyr Thr Ile
660 665 670

Asp Phe Ala Ala Lys Gln Gly Asn Gly Lys Ile Glu His Leu Lys Ser
675 680 685

Pro Glu Leu Asn Val Asp Leu Ala Ala Ala Asp Ile Lys Pro Asp Gly
690 695 700

Lys Arg His Ala Val Ile Ser Gly Ser Val Leu Tyr Asn Gln Ala Glu
705 710 715 720

Lys Gly Ser Tyr Ser Leu Gly Ile Phe Gly Gly Lys Ala Gln Glu Val
725 730 735

Ala Gly Ser Ala Glu Val Lys Thr Val Asn Gly Ile Arg His Ile Gly
740 745 750

Leu Ala Ala Lys Gln
755

<210> SEQ ID NO 33
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (32)..(32)
<223> OTHER INFORMATION: Any amino acid except Ser
<220> FEATURE:
<221> NAME/KEY: MOD_RES
<222> LOCATION: (123)..(123)
<223> OTHER INFORMATION: Any amino acid except Leu
<220> FEATURE:
<221> NAME/KEY: MOD_RES
<222> LOCATION: (285)..(285)
<223> OTHER INFORMATION: Any amino acid except Ser
<220> FEATURE:
<221> NAME/KEY: MOD_RES
<222> LOCATION: (379)..(379)
<223> OTHER INFORMATION: Any amino acid except Leu -continued

<400> SEQUENCE: 33

Val Ala Ala Asp Ile Gly Ala Gly Leu Ala Asp Ala Leu Thr Ala Pro
1 5 10 15

Leu Asp His Lys Asp Lys Ser Leu Gln Ser Leu Thr Leu Asp Gln Xaa
20 25 30

Val Arg Lys Asn Glu Lys Leu Lys Leu Ala Ala Gln Gly Ala Glu Lys
35 40 45

Thr Tyr Gly Asn Gly Asp Ser Leu Asn Thr Gly Lys Leu Lys Asn Asp
50 55 60

Lys Val Ser Arg Phe Asp Phe Ile Arg Gln Ile Glu Val Asp Gly Gln
65 70 75 80

Leu Ile Thr Leu Glu Ser Gly Glu Phe Gln Ile Tyr Lys Gln Asp His
85 90 95

Ser Ala Val Val Ala Leu Gln Ile Glu Lys Ile Asn Asn Pro Asp Lys
100 105 110

Ile Asp Ser Leu Ile Asn Gln Arg Ser Phe Xaa Val Ser Gly Leu Gly
115 120 125

Gly Glu His Thr Ala Phe Asn Gln Leu Pro Asp Gly Lys Ala Glu Tyr
130 135 140

His Gly Lys Ala Phe Ser Ser Asp Asp Ala Gly Gly Lys Leu Thr Tyr
145 150 155 160

Thr Ile Asp Phe Ala Ala Lys Gln Gly His Gly Lys Ile Glu His Leu
165 170 175

Lys Thr Pro Glu Gln Asn Val Glu Leu Ala Ala Ala Glu Leu Lys Ala
180 185 190

Asp Glu Lys Ser His Ala Val Ile Leu Gly Asp Thr Arg Tyr Gly Ser
195 200 205

Glu Glu Lys Gly Thr Tyr His Leu Ala Leu Phe Gly Asp Arg Ala Gln
210 215 220

Glu Ile Ala Gly Ser Ala Thr Val Lys Ile Gly Glu Lys Val His Glu
225 230 235 240

Ile Gly Ile Ala Gly Lys Gln Gly Ser Gly Gly Gly Gly Val Ala Ala
245 250 255

Asp Ile Gly Thr Gly Leu Ala Asp Ala Leu Thr Ala Pro Leu Asp His
260 265 270

Lys Asp Lys Gly Leu Lys Ser Leu Thr Leu Glu Asp Xaa Ile Pro Gln
275 280 285

Asn Gly Thr Leu Thr Leu Ser Ala Gln Gly Ala Glu Lys Thr Phe Lys
290 295 300

Ala Gly Asp Lys Asp Asn Ser Leu Asn Thr Gly Lys Leu Lys Asn Asp
305 310 315 320

Lys Ile Ser Arg Phe Asp Phe Val Gln Lys Ile Glu Val Asp Gly Gln
325 330 335

Thr Ile Thr Leu Ala Ser Gly Glu Phe Gln Ile Tyr Lys Gln Asn His
340 345 350

Ser Ala Val Val Ala Leu Gln Ile Glu Lys Ile Asn Asn Pro Asp Lys
355 360 365

Thr Asp Ser Leu Ile Asn Gln Arg Ser Phe Xaa Val Ser Gly Leu Gly
370 375 380

Gly Glu His Thr Ala Phe Asn Gln Leu Pro Gly Gly Lys Ala Glu Tyr
385 390 395 400

His Gly Lys Ala Phe Ser Ser Asp Asp Pro Asn Gly Arg Leu His Tyr

```
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
            740                 745                 750

Leu Ala Ala Lys Gln
        755
```

<210> SEQ ID NO 34
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415
```

```
Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
            740                 745                 750

Leu Ala Ala Lys Gln
        755
```

<210> SEQ ID NO 35
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (32)..(32)
<223> OTHER INFORMATION: Any amino acid except Ser
<220> FEATURE:
<221> NAME/KEY: MOD_RES
<222> LOCATION: (123)..(123)
<223> OTHER INFORMATION: Any amino acid except Leu
<220> FEATURE:
<221> NAME/KEY: MOD_RES
<222> LOCATION: (285)..(285)
<223> OTHER INFORMATION: Any amino acid except Ser
<220> FEATURE:
<221> NAME/KEY: MOD_RES
<222> LOCATION: (379)..(379)
<223> OTHER INFORMATION: Any amino acid except Leu
<220> FEATURE:
<221> NAME/KEY: MOD_RES
<222> LOCATION: (543)..(543)
<223> OTHER INFORMATION: Any amino acid except Arg

<400> SEQUENCE: 35

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Xaa
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Xaa Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Xaa Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320
```

-continued

```
Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Xaa Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Xaa Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
```

```
            740                 745                 750

Leu Ala Ala Lys Gln
        755


<210> SEQ ID NO 36
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335
```

```
Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Ser Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
            740                 745                 750
```

Leu Ala Ala Lys Gln
        755

<210> SEQ ID NO 37
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Ala
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His

-continued

```
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Ala
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Ser Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
            740                 745                 750

Leu Ala Ala Lys Gln
        755
```

<210> SEQ ID NO 38
<211> LENGTH: 769
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 38

Met Gly Pro Asp Ser Asp Arg Leu Gln Gln Arg Arg Val Ala Ala Asp
1 5 10 15

Ile Gly Ala Gly Leu Ala Asp Ala Leu Thr Ala Pro Leu Asp His Lys
20 25 30

Asp Lys Ser Leu Gln Ser Leu Thr Leu Asp Gln Val Val Arg Lys Asn
35 40 45

Glu Lys Leu Lys Leu Ala Ala Gln Gly Ala Glu Lys Thr Tyr Gly Asn
50 55 60

Gly Asp Ser Leu Asn Thr Gly Lys Leu Lys Asn Asp Lys Val Ser Arg
65 70 75 80

Phe Asp Phe Ile Arg Gln Ile Glu Val Asp Gly Gln Leu Ile Thr Leu
85 90 95

Glu Ser Gly Glu Phe Gln Ile Tyr Lys Gln Asp His Ser Ala Val Val
100 105 110

Ala Leu Gln Ile Glu Lys Ile Asn Asn Pro Asp Lys Ile Asp Ser Leu
115 120 125

Ile Asn Gln Arg Ser Phe Arg Val Ser Gly Leu Gly Gly Glu His Thr
130 135 140

Ala Phe Asn Gln Leu Pro Asp Gly Lys Ala Glu Tyr His Gly Lys Ala
145 150 155 160

Phe Ser Ser Asp Asp Ala Gly Gly Lys Leu Thr Tyr Thr Ile Asp Phe
165 170 175

Ala Ala Lys Gln Gly His Gly Lys Ile Glu His Leu Lys Thr Pro Glu
180 185 190

Gln Asn Val Glu Leu Ala Ala Ala Glu Leu Lys Ala Asp Glu Lys Ser
195 200 205

His Ala Val Ile Leu Gly Asp Thr Arg Tyr Gly Ser Glu Glu Lys Gly
210 215 220

Thr Tyr His Leu Ala Leu Phe Gly Asp Arg Ala Gln Glu Ile Ala Gly
225 230 235 240

Ser Ala Thr Val Lys Ile Gly Glu Lys Val His Ala Ile Gly Ile Ala
245 250 255

Gly Lys Gln Gly Ser Gly Gly Gly Gly Val Ala Ala Asp Ile Gly Thr
260 265 270

Gly Leu Ala Asp Ala Leu Thr Ala Pro Leu Asp His Lys Asp Lys Gly
275 280 285

Leu Lys Ser Leu Thr Leu Glu Asp Val Ile Pro Gln Asn Gly Thr Leu
290 295 300

Thr Leu Ser Ala Gln Gly Ala Glu Lys Thr Phe Lys Ala Gly Asp Lys
305 310 315 320

Asp Asn Ser Leu Asn Thr Gly Lys Leu Lys Asn Asp Lys Ile Ser Arg
325 330 335

Phe Asp Phe Val Gln Lys Ile Glu Val Asp Gly Gln Thr Ile Thr Leu
340 345 350

```
Ala Ser Gly Glu Phe Gln Ile Tyr Lys Gln Asn His Ser Ala Val Val
        355                 360                 365

Ala Leu Gln Ile Glu Lys Ile Asn Asn Pro Asp Lys Thr Asp Ser Leu
    370                 375                 380

Ile Asn Gln Arg Ser Phe Arg Val Ser Gly Leu Gly Gly Glu His Thr
385                 390                 395                 400

Ala Phe Asn Gln Leu Pro Gly Gly Lys Ala Glu Tyr His Gly Lys Ala
                405                 410                 415

Phe Ser Ser Asp Asp Pro Asn Gly Arg Leu His Tyr Ser Ile Asp Phe
            420                 425                 430

Thr Lys Lys Gln Gly Tyr Gly Arg Ile Glu His Leu Lys Thr Leu Glu
        435                 440                 445

Gln Asn Val Glu Leu Ala Ala Ala Glu Leu Lys Ala Asp Glu Lys Ser
    450                 455                 460

His Ala Val Ile Leu Gly Asp Thr Arg Tyr Gly Ser Glu Glu Lys Gly
465                 470                 475                 480

Thr Tyr His Leu Ala Leu Phe Gly Asp Arg Ala Gln Glu Ile Ala Gly
                485                 490                 495

Ser Ala Thr Val Lys Ile Gly Glu Lys Val His Ala Ile Gly Ile Ala
            500                 505                 510

Gly Lys Gln Gly Ser Gly Gly Gly Gly Val Ala Ala Asp Ile Gly Ala
        515                 520                 525

Gly Leu Ala Asp Ala Leu Thr Ala Pro Leu Asp His Lys Asp Lys Gly
    530                 535                 540

Leu Gln Ser Leu Thr Leu Asp Gln Ser Val Ser Lys Asn Glu Lys Leu
545                 550                 555                 560

Lys Leu Ala Ala Gln Gly Ala Glu Lys Thr Tyr Gly Asn Gly Asp Ser
                565                 570                 575

Leu Asn Thr Gly Lys Leu Lys Asn Asp Lys Val Ser Arg Phe Asp Phe
            580                 585                 590

Ile Arg Gln Ile Glu Val Asp Gly Gln Leu Ile Thr Leu Glu Ser Gly
        595                 600                 605

Glu Phe Gln Val Tyr Lys Gln Ser His Ser Ala Leu Thr Ala Phe Gln
    610                 615                 620

Thr Glu Gln Ile Gln Asp Ser Glu His Ser Gly Lys Met Val Ala Lys
625                 630                 635                 640

Arg Gln Phe Arg Ile Gly Asp Ile Ala Gly Glu His Thr Ser Phe Asp
                645                 650                 655

Lys Leu Pro Glu Gly Gly Arg Ala Thr Tyr Arg Gly Thr Ala Phe Gly
            660                 665                 670

Ser Asp Asp Ala Gly Gly Lys Leu Thr Tyr Thr Ile Asp Phe Ala Ala
        675                 680                 685

Lys Gln Gly Asn Gly Lys Ile Glu His Leu Lys Ser Pro Glu Leu Asn
    690                 695                 700

Val Asp Leu Ala Ala Ala Asp Ile Lys Pro Asp Gly Lys Arg His Ala
705                 710                 715                 720

Val Ile Ser Gly Ser Val Leu Tyr Asn Gln Ala Glu Lys Gly Ser Tyr
                725                 730                 735

Ser Leu Gly Ile Phe Gly Gly Lys Ala Gln Glu Val Ala Gly Ser Ala
            740                 745                 750

Glu Val Lys Thr Val Asn Gly Ile Arg His Ile Gly Leu Ala Ala Lys
        755                 760                 765

Gln
```

<210> SEQ ID NO 39
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:
<221> NAME/KEY: MOD_RES
<222> LOCATION: (123)..(123)
<223> OTHER INFORMATION: Any amino acid except Leu
<220> FEATURE:
<221> NAME/KEY: MOD_RES
<222> LOCATION: (379)..(379)
<223> OTHER INFORMATION: Any amino acid except Leu

<400> SEQUENCE: 39

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Xaa Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Ser Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
```

-continued

```
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Xaa Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735
```

Ala Gly Ser Ala Glu Val Lys Thr Val Asn Gly Ile Arg His Ile Gly
740 745 750

Leu Ala Ala Lys Gln
755

<210> SEQ ID NO 40
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Val Ala Ala Asp Ile Gly Ala Gly Leu Ala Asp Ala Leu Thr Ala Pro
1 5 10 15

Leu Asp His Lys Asp Lys Ser Leu Gln Ser Leu Thr Leu Asp Gln Ser
20 25 30

Val Arg Lys Asn Glu Lys Leu Lys Leu Ala Ala Gln Gly Ala Glu Lys
35 40 45

Thr Tyr Gly Asn Gly Asp Ser Leu Asn Thr Gly Lys Leu Lys Asn Asp
50 55 60

Lys Val Ser Arg Phe Asp Phe Ile Arg Gln Ile Glu Val Asp Gly Gln
65 70 75 80

Leu Ile Thr Leu Glu Ser Gly Glu Phe Gln Ile Tyr Lys Gln Asp His
85 90 95

Ser Ala Val Val Ala Leu Gln Ile Glu Lys Ile Asn Asn Pro Asp Lys
100 105 110

Ile Asp Ser Leu Ile Asn Gln Arg Ser Phe Arg Val Ser Gly Leu Gly
115 120 125

Gly Glu His Thr Ala Phe Asn Gln Leu Pro Asp Gly Lys Ala Glu Tyr
130 135 140

His Gly Lys Ala Phe Ser Ser Asp Asp Ala Gly Gly Lys Leu Thr Tyr
145 150 155 160

Thr Ile Asp Phe Ala Ala Lys Gln Gly His Gly Lys Ile Glu His Leu
165 170 175

Lys Thr Pro Glu Gln Asn Val Glu Leu Ala Ala Ala Glu Leu Lys Ala
180 185 190

Asp Glu Lys Ser His Ala Val Ile Leu Gly Asp Thr Arg Tyr Gly Ser
195 200 205

Glu Glu Lys Gly Thr Tyr His Leu Ala Leu Phe Gly Asp Arg Ala Gln
210 215 220

Glu Ile Ala Gly Ser Ala Thr Val Lys Ile Gly Glu Lys Val His Glu
225 230 235 240

Ile Gly Ile Ala Gly Lys Gln Gly Ser Gly Gly Gly Gly Val Ala Ala
245 250 255

Asp Ile Gly Thr Gly Leu Ala Asp Ala Leu Thr Ala Pro Leu Asp His
260 265 270

Lys Asp Lys Gly Leu Lys Ser Leu Thr Leu Glu Asp Ser Ile Pro Gln
275 280 285

Asn Gly Thr Leu Thr Leu Ser Ala Gln Gly Ala Glu Lys Thr Phe Lys
290 295 300

Ala Gly Asp Lys Asp Asn Ser Leu Asn Thr Gly Lys Leu Lys Asn Asp
305 310 315 320

-continued

```
Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
```

```
            740                 745                 750

Leu Ala Ala Lys Gln
        755


<210> SEQ ID NO 41
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Ser Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335
```

```
Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Ser Lys
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Gln Leu Ile Thr
            580                 585                 590

Leu Glu Ser Gly Glu Phe Gln Val Tyr Lys Gln Ser His Ser Ala Leu
        595                 600                 605

Thr Ala Phe Gln Thr Glu Gln Ile Gln Asp Ser Glu His Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly Asn Gly Lys Ile Glu His Leu Lys Ser
        675                 680                 685

Pro Glu Leu Asn Val Asp Leu Ala Ala Ala Asp Ile Lys Pro Asp Gly
    690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Gly Lys Ala Gln Glu Val
                725                 730                 735

Ala Gly Ser Ala Glu Val Lys Thr Val Asn Gly Ile Arg His Ile Gly
            740                 745                 750
```

Leu Ala Ala Lys Gln
755

<210> SEQ ID NO 42
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (3)..(10)
<223> OTHER INFORMATION: /replace=" "
<220> FEATURE:
<221> NAME/KEY: misc_feature
<222> LOCATION: (1)..(10)
<223> OTHER INFORMATION: /note="Variant residues given in the sequence have no preference with respect to those in the annotations for variant positions"

<400> SEQUENCE: 42

Gly Gly Gly Gly Gly Gly Gly Gly Gly Gly
1 5 10

<210> SEQ ID NO 43
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(10)
<223> OTHER INFORMATION: /replace=" "
<220> FEATURE:
<221> NAME/KEY: misc_feature
<222> LOCATION: (1)..(10)
<223> OTHER INFORMATION: /note="Variant residues given in the sequence have no preference with respect to those in the annotations for variant positions"

<400> SEQUENCE: 43

His His His His His His His His His His
1 5 10

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (5)..(10)
<223> OTHER INFORMATION: /replace=" "
<220> FEATURE:
<221> NAME/KEY: misc_feature
<222> LOCATION: (1)..(10)
<223> OTHER INFORMATION: /note="Variant residues given in the sequence have no preference with respect to those in the annotations for variant positions"

<400> SEQUENCE: 44

His His His His His His His His His His
1 5 10